United States Patent

Nohira et al.

[11] Patent Number: 4,918,213
[45] Date of Patent: Apr. 17, 1990

[54] OPTICALLY ACTIVE COMPOUND AND LIQUID CRYSTAL COMPOSITION CONTAINING SAME

[75] Inventors: Hiroyuki Nohira, Urawa; Masanao Kamei, Annaka; Hideki Kanazawa, Yotsukaichi; Yoko Yamada, Atsugi; Yuko Etoh, Tokorozawa, all of Japan

[73] Assignee: Canon Kabushiki Kaisha, Tokyo, Japan

[21] Appl. No.: 223,363

[22] Filed: Jul. 25, 1988

[30] Foreign Application Priority Data

Jul. 28, 1987 [JP] Japan .................. 62-186575
Aug. 18, 1987 [JP] Japan .................. 62-204343
Feb. 24, 1988 [JP] Japan .................. 63-041456
Mar. 25, 1988 [JP] Japan .................. 63-071034

[51] Int. Cl.$^4$ .............. G02F 1/13; C09K 19/34; C07D 239/02; C07C 69/76; C07C 43/20; C07C 43/02; C07C 41/00
[52] U.S. Cl. ................ 558/271; 350/350 R; 350/350 S; 558/273; 558/275; 558/276; 560/8; 560/55; 560/60; 560/61; 560/64; 560/65; 560/130; 560/146; 568/647; 568/661; 544/242; 544/315; 544/318; 544/335; 252/299.6; 252/299.61; 252/299.63; 252/299.64; 252/299.65; 252/299.66; 252/299.67; 252/299.5
[58] Field of Search ............. 558/271, 273, 275, 276; 560/130, 8, 55, 60, 61, 64, 65, 146; 568/647, 661

[56] References Cited

U.S. PATENT DOCUMENTS

| | | | |
|---|---|---|---|
| 4,621,901 | 11/1986 | Petrzilka et al. | 544/315 |
| 4,623,477 | 11/1986 | Ogawa et al. | 544/315 |
| 4,713,197 | 12/1987 | Eidenschink et al. | 544/315 |
| 4,776,973 | 10/1988 | Bofinger et al. | 544/315 |

FOREIGN PATENT DOCUMENTS

| | | | |
|---|---|---|---|
| 0213841 | 3/1987 | European Pat. Off. | 558/271 |
| 0224725 | 6/1987 | European Pat. Off. | 558/271 |
| 3525015 | 1/1986 | Fed. Rep. of Germany | 558/271 |
| 1603076 | 11/1981 | United Kingdom | 558/271 |

Primary Examiner—Mary C. Lee
Assistant Examiner—J. Richter

Attorney, Agent, or Firm—Fitzpatrick, Cella, Harper & Scinto

[57] ABSTRACT

An optically active, generally mesomorphic compound represented by the following formula (I):

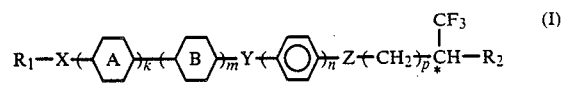

wherein $R_1$ denotes an alkyl group having 1-18 carbon atoms, $R_2$ denotes an alkyl group having 1-12 carbon atoms; X denotes a single bond, —O—,

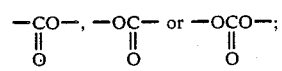

Y denotes a single bond,

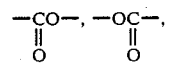

—CH$_2$O— or —OCH$_2$—; Z denotes —OCH$_2$—,

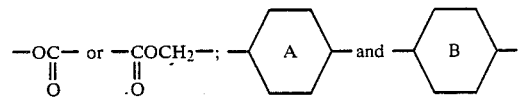

respectively denotes

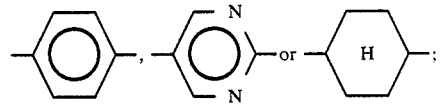

C* denotes an asymmetric carbon atom; k, m and n are respectively 0, 1 or 2 with proviso that k+m+n amounts to 2 or 3; and p is 1 or 2.

10 Claims, No Drawings

OPTICALLY ACTIVE COMPOUND AND LIQUID CRYSTAL COMPOSITION CONTAINING SAME

FIELD OF THE INVENTION AND RELATED ART

The present invention relates to a novel optically active compound, a liquid crystal composition containing the same and a liquid crystal device using the liquid crystal composition. More specifically, the present invention relates to an optically active compound having a trifluoromethyl group attached to the asymmetric carbon atom, a liquid crystal composition containing the same and a liquid crystal device using the liquid crystal composition.

There has been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971), pp. 127–128. In this type of liquid crystal devices, the number of picture elements have been restricted, because there is a problem that a crosstalk phenomenon occurs when a device of a matrix electrode structure with a high density of picture elements is driven according to a multiplexing driving scheme. Further, their uses for display have been limited because of slow electric field response and poor visual angle characteristics.

As another type of liquid crystal device, there has been known one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned draw-backs of the conventional types of liquid crystal devices, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4,367,924). As the bistable liquid crystal, a ferroelectric liquid crystal showing a chiral smectic C phase (SmC*) or H phase (SmH*) is generally used.

Such a ferroelectric liquid crystal has very rapid response speed on account of having spontaneous polarization, can also exhibit memorizable bistable state and further have excellent vision angle characteristic, and therefore it is suitable for a display of large capacity and large picture area.

Further, since a material used as a ferroelectric liquid crystal has an asymmetry, it can be used as a functional material to be used in the following types of optical devices in addition to the use as a ferroelectric liquid crystal material:

(1) Those utilizing a cholesteric-nematic phase transition in a liquid crystal state (J. J. Wysoki, A. Adams and W. Haas: Phys. Rev. Lett., 20, 10204 1968);

(2) Those utilizing a guest-host effect of the White-Taylor type in a liquid crystal state (D. L. White and G. N. Taylor: J. Appl. Phys. 45, 4718 (1974)).

These optical devices are important as display devices and modulation devices, while the explanation of the individual systems is left to the respective references and omitted.

It has been understood that, in a method utilizing an electric field-responsive optical effect of a liquid crystal, it is desirable to introduce a polar group or a group providing a polar bond in a compound constituting the liquid crystal in order to enhance the responsive characteristic of the liquid crystal. Particularly, with respect to a ferroelectric liquid crystal, it has been known that the responsive speed is proportional to its spontaneous polarization, so that it is desired to increase the spontaneous polarization in order to realize a high response speed. From this viewpoint, P. Keller et al have shown that it is possible to provide a higher response speed by introducing a chlorine atom directly connected to an asymmetric carbon atom. However, such a chlorine atom directly introduced to an asymmetric carbon atom involves problems that it is chemically unstable and lowers the stability of a liquid crystal phase as it has a large atomic radius.

On the other hand, many of optically active functional compounds for use in optical devices as described above are synthesized through an intermediate which per se is optically active. Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives. However, it has been seldome to incorporate a polar group into such an intermediate. Partly for this reason, the above mentioned method of introducing a polar group directly to an asymmetric carbon atom has not been utilized very effectively.

SUMMARY OF THE INVENTION

A principal object of the present invention is, in view of the above problems, to provide a compound having an enhanced polarity by introducing a trifluoromethyl group, which is stable and has a large dipole moment, directly to an asymmetric carbon atom.

Another object of the present invention is to provide a liquid crystal composition containing at least one species of the optically active compound, and a liquid crystal device using the liquid crystal composition.

According to a principal aspect of the present invention, there is provided a compound (trifluoroalkane derivative) represented by the following formula (I):

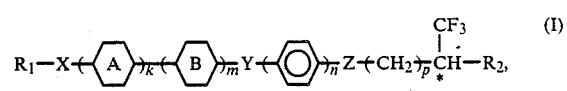

wherein $R_1$ denotes an alkyl group having 1–18 carbon atoms, $R_2$ denotes an alkyl group having 1–12 carbon atoms; X denotes a single bond, —O—,

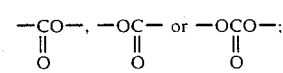

Y denotes a single bond,

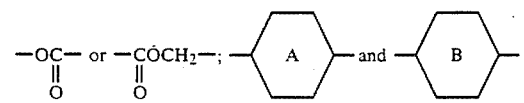

—CH$_2$O— or —OCH$_2$—; Z denotes —OCH$_2$—,

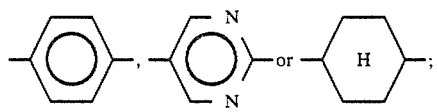

respectively denotes

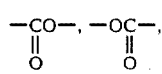

C* denotes an asymmetric carbon atom; k, m and n are respectively 0, 1 or 2 with proviso that k+m+n amounts to 2 or 3; and p is 1 or 2.

The present invention further provides a liquid crystal composition containing at least one species of the above-mentioned optically active and also a liquid crystal device using the liquid crystal composition.

Among the compounds represented by the above formula (I), those represented by the following formula (I-a), (I-b) or (I-c) show better results.

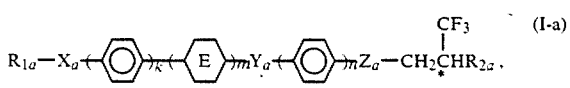

wherein R$_{1a}$ denotes an alkyl group having 4–16 carbon atoms, R$_{2a}$ denotes an alkyl group having 1–12 carbon atoms; k, m and n are respectively 0, 1 or 2 with proviso that k+m+n amounts to 2 or 3; X$_a$ denotes a single bond; Y$_a$ denotes a single bond or

Z$_a$ denotes —OCH$_2$—,

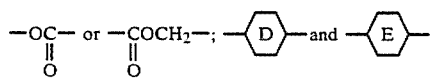

respectively denote

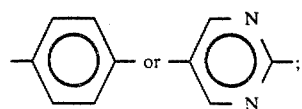

and C* denotes an asymmetric carbon atom;

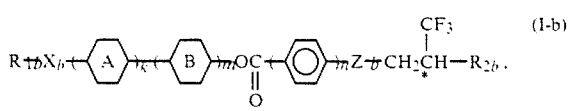

wherein R$_{1b}$ denotes an alkyl group having 1–18 carbon atoms, R$_{2b}$ denotes an alkyl group having 1–12 carbon atoms; X$_b$ denotes a single bond, —O—,

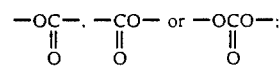

Z$_b$ denotes —OCH$_2$— or

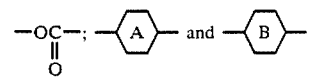

respectively denote

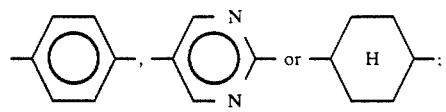

k, m and n are respectively 0, 1 or 2 with proviso that k+m+n amounts to 2 or 3; and C* denotes an asymmetric carbon atom.

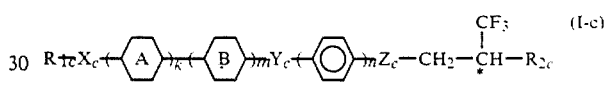

wherein R$_{1c}$ denotes an alkyl group having 1–18 carbon atoms, R$_{2c}$ denotes an alkyl group having 1–12 carbon atoms; X$_c$ denotes a single bond, —O—,

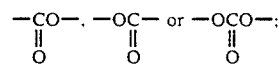

Y$_c$ denotes —CH$_2$O— or —OCH$_2$—; Z$_c$ denotes —OCH$_2$— or

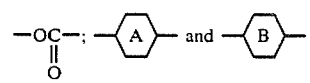

respectively denotes

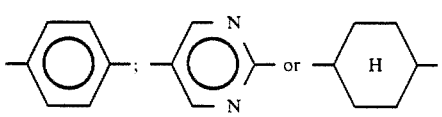

C* denotes an asymmetric carbon atom; and k, m and n are respectively 0, 1 or 2 with proviso that k+m+n amounts to 2 or 3.

DESCRIPTION OF PREFERRED EMBODIMENTS

The compounds represented by the above-mentioned formula (I) may preferably be produced through optical intermediates such as 3-trifluoromethyl alkanoic acid of the formula (II) below and 3-trifluoromethyl-1-alkanol of the formula (III) as disclosed in Japanese Patent Application Nos. 183,485/1987, and 37624/1988:

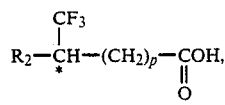 (II)

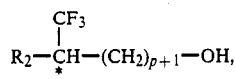 (III)

wherein $R_2$ denotes an alkyl group having 1-12 carbon atoms, and p is 1 or 2.

Some representative reaction schemes for producing the compounds represented by the formula (I) through these intermediates are shown below.

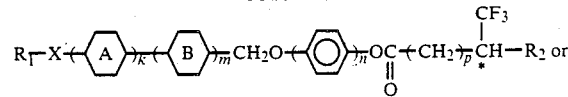

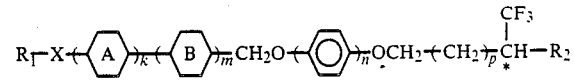

② Case where M is —CO—,

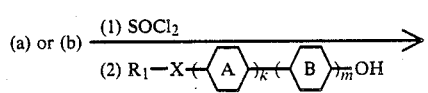

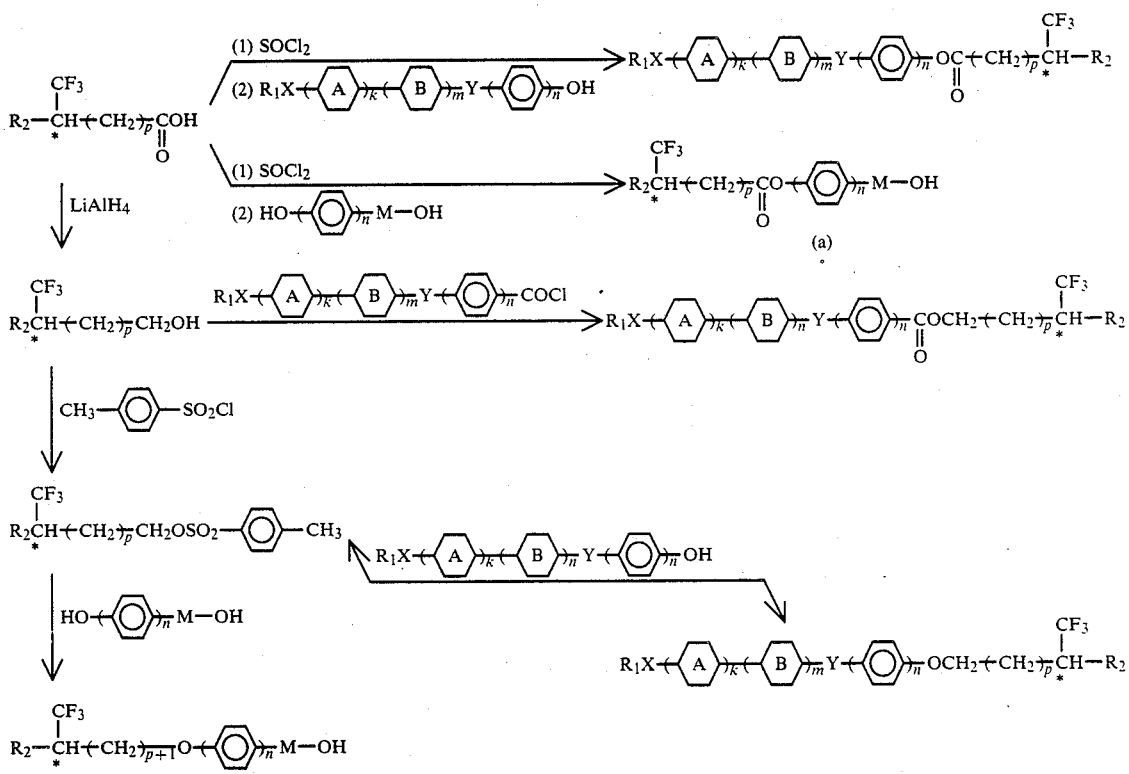

From the compound of the formula (a) or (b), the following reactions are further conducted:

① Case where M is a single bond

①-1 (a) or (b) 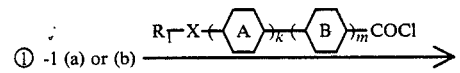

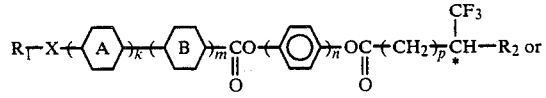 or

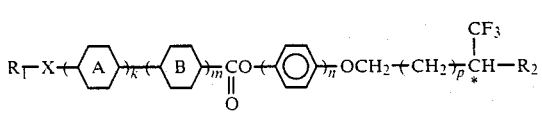

①-2 (a) or (b) 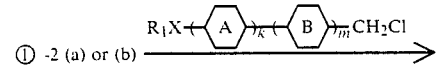

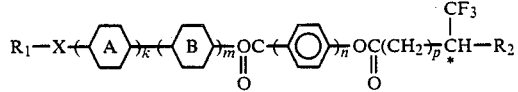

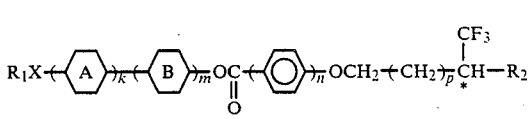

③ Case where M is —CH$_2$—, (a) or (b) 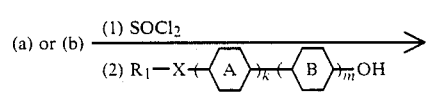

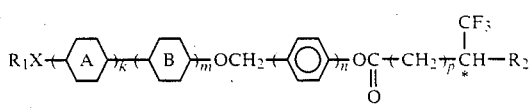

-continued

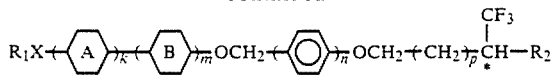

In the above series of formulas, $R_1$ denotes an alkyl group having 1-18 carbon atoms, $R_2$ denotes an alkyl group having 1-12 carbon atoms; X denotes a single bond, —O—,

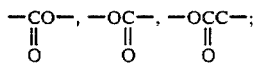

Y denotes a single bond,

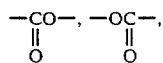

—CH$_2$O—, or —OCH$_2$—;

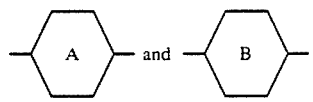

respectively denotes

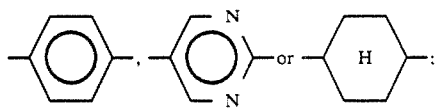

C* denotes an asymmetric carbon atom; k, m and n are respectively 0, 1 or 2 with proviso that k+m+n amounts to 2 or 3; and p is 1 or 2.

Hereinbelow, some examples of the compound represented by the formula (I) are enumerated.

Example Compound

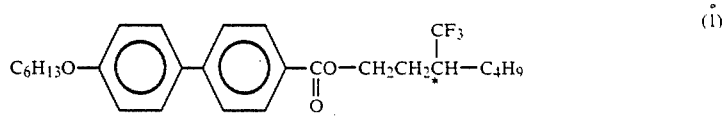

(1)

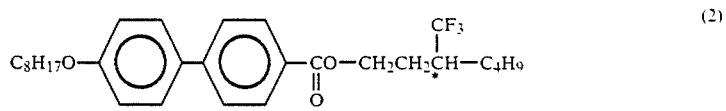

(2)

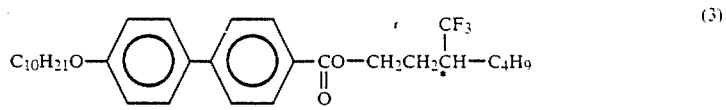

(3)

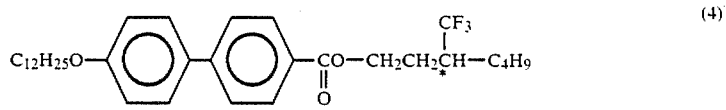

(4)

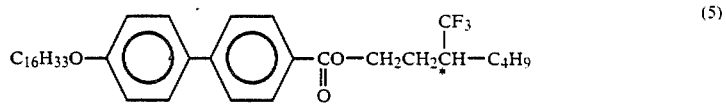

(5)

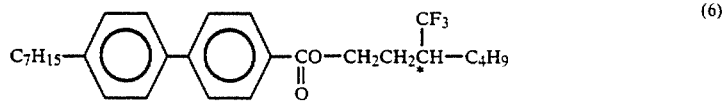

(6)

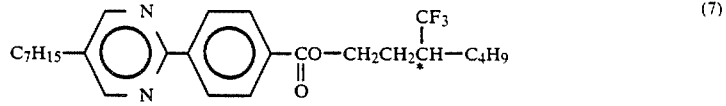

(7)

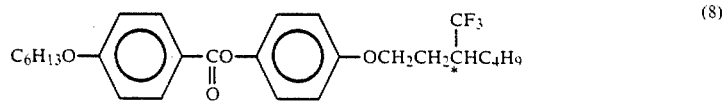

(8)

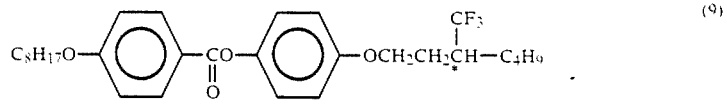

(9)

-continued
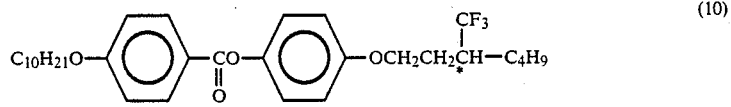 (10)
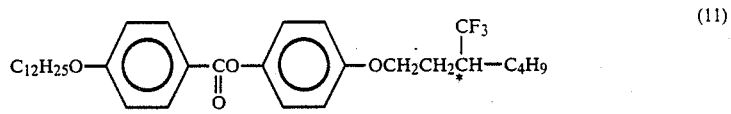 (11)
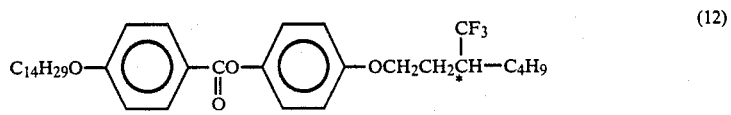 (12)
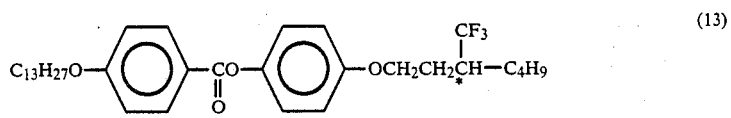 (13)
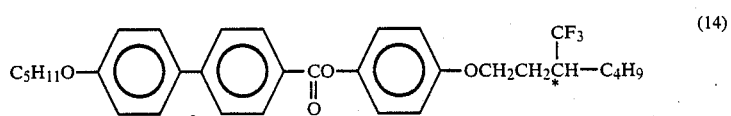 (14)
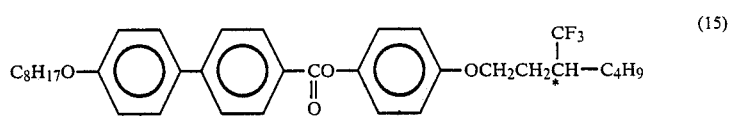 (15)
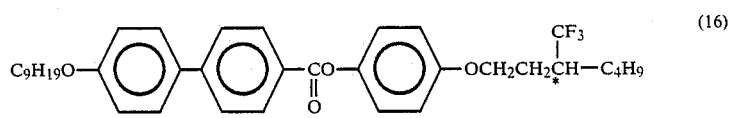 (16)
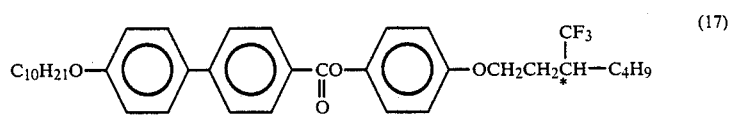 (17)
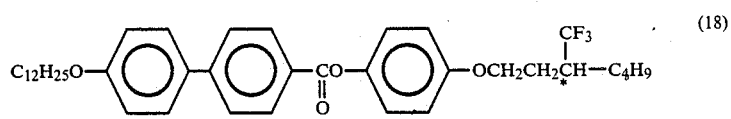 (18)
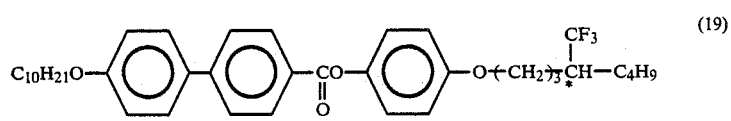 (19)
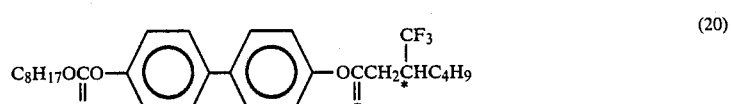 (20)
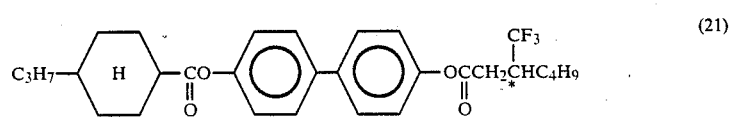 (21)
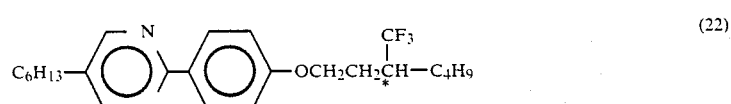 (22)

-continued
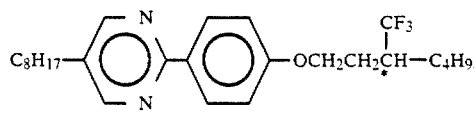 (23)
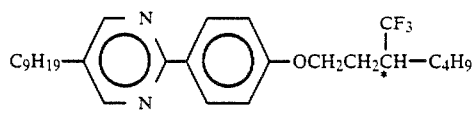 (24)
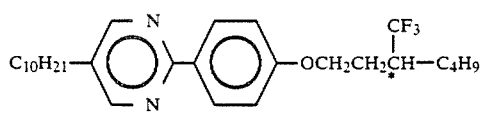 (25)
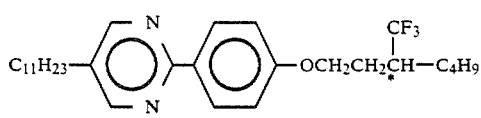 (26)
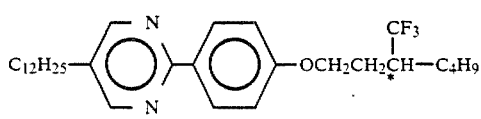 (27)
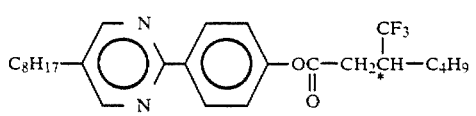 (28)
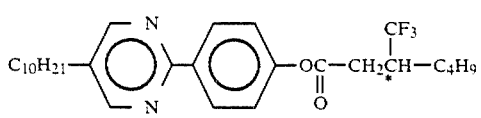 (29)
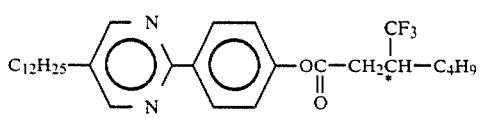 (30)
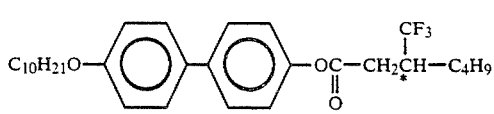 (31)
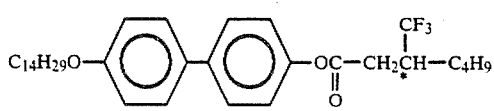 (32)
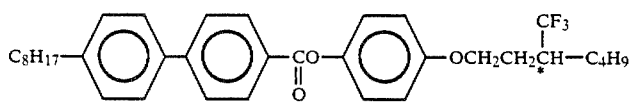 (33)
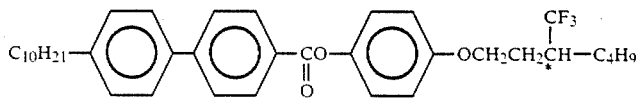 (34)
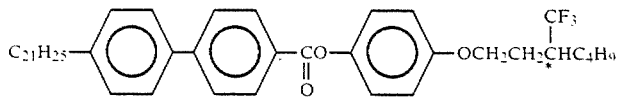 (35)

-continued
 (36)
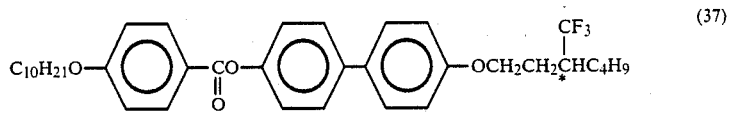 (37)
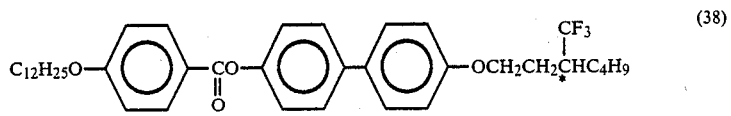 (38)
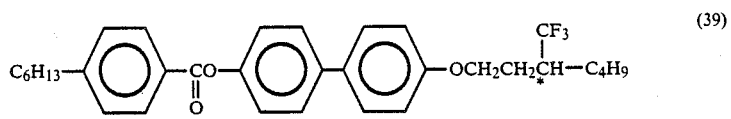 (39)
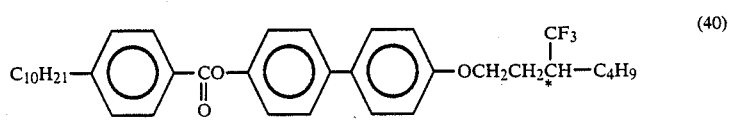 (40)
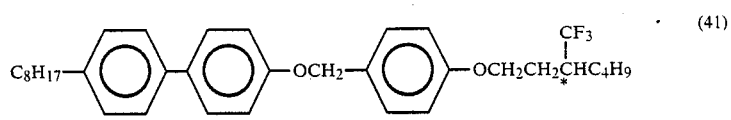 (41)
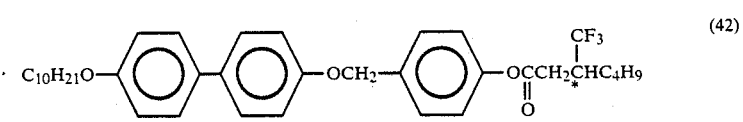 (42)
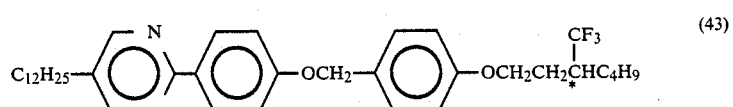 (43)
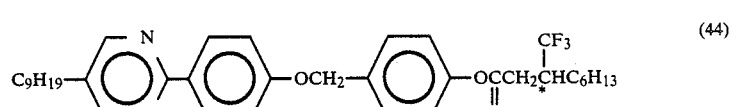 (44)
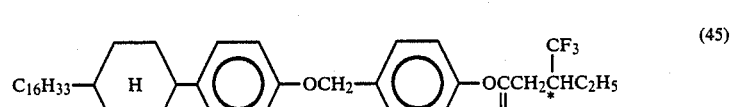 (45)
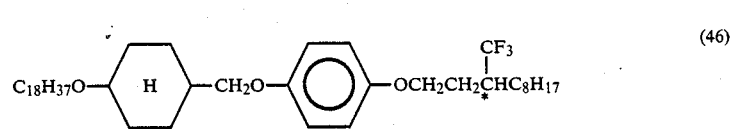 (46)
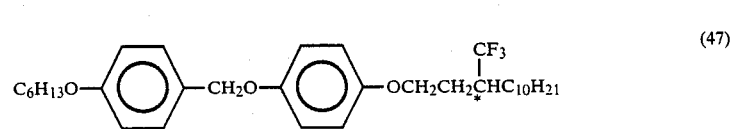 (47)
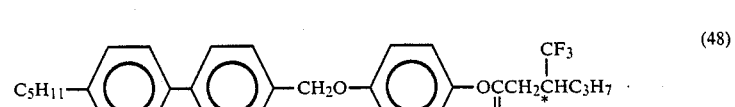 (48)

-continued

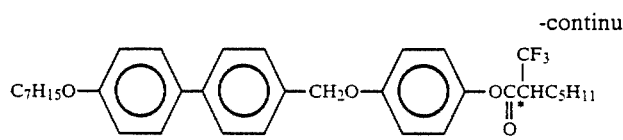 (49)

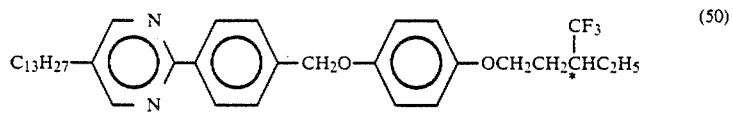 (50)

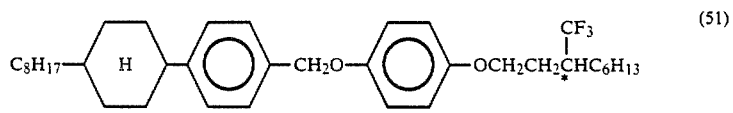 (51)

The liquid crystal composition according to the present invention contains at least one species of the trifluoroalkane derivative represented by the formula (I). For example, the trifluoroalkane derivative represented by the formula (I) may be mised with a ferroelectric liquid crystal selected from those of the formulas (1)–(13) shown below to increase the spontaneous polarization and increase the response speed. In this case, it is preferred to use the trifluoroalkane derivative represent by the formula (I) in an amount constituting 0.1–99 wt. %, particularly 1–90 wt. %, of the resulting liquid crystal composition.

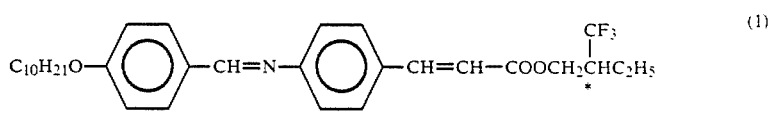 (1)

p-decyloxybenzylidene-p'-amino-2-methylbutylcinnamate
(DOBAMBC)

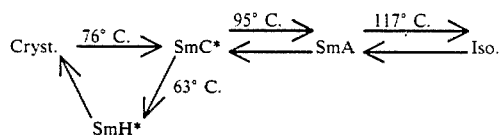

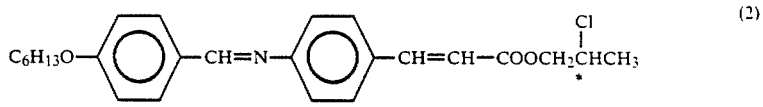 (2)

p-hexyloxybenzylidene-p'-amino-2-chloropropylcinnamate
(HOBACPC)

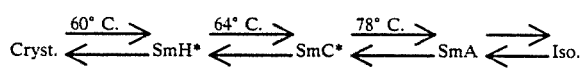

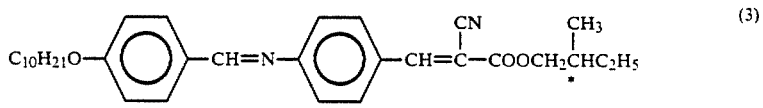 (3)

p-decyloxybenzylidene-p'-amino-2-methylbutyl-α-
cyanocinnamate (DOBAMBCC)

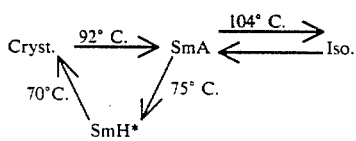

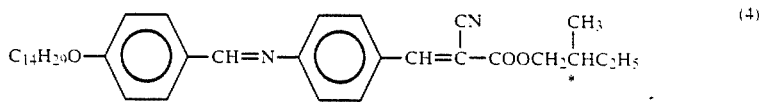 (4)

p-tetradecyloxybenzylidene-p'-amino-2-methylbutyl-

-continued
α-cyanocinnamate (TDOBAMBCC)

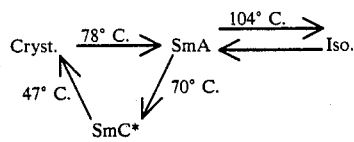

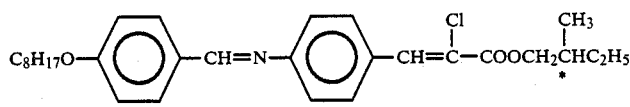 (5)

p-octyloxybenzylidene-p'-amino-2-methylbutyl-α-chlorocinnamate (OOBAMBCC)

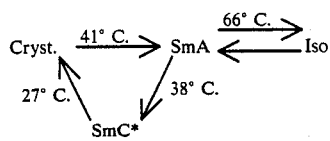

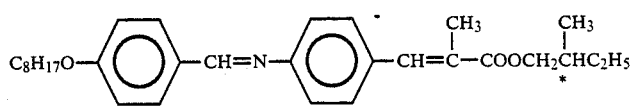 (6)

p-octyloxybenzylidene-p'-amino-2-methylbutyl-α-methylcinnamate

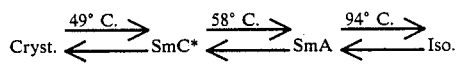

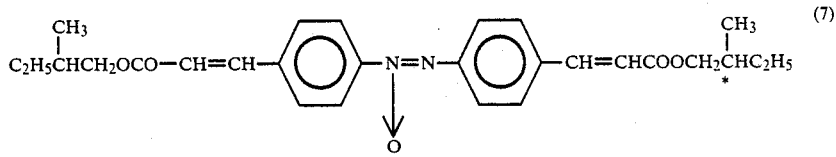 (7)

4,4'-azoxycinnamic acid-bis(2-methylbutyl)ester

Cryst. $\xleftrightarrow{121° C.}$ SmC* $\xleftrightarrow{134° C.}$ SmA $\xleftrightarrow{168° C.}$ Iso.

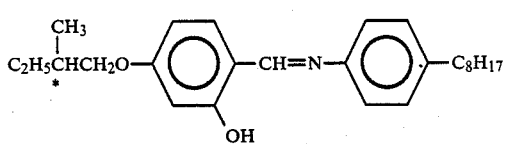 (8)

4-O-(2-methylbutyl)resorcylidene-4'-octylaniline (MBRA 8)

Cryst. $\xleftrightarrow{28° C.}$ SmC* $\xleftrightarrow{55° C.}$ SmA $\xleftrightarrow{62° C.}$ Iso.

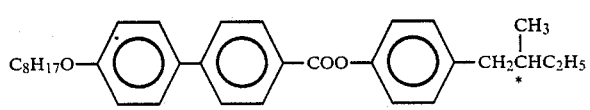 (9)

4-(2'-methylbutyl)phenyl-4'-octyloxybiphenyl-4-carboxylate

Cryst. $\xleftrightarrow{78° C.}$ Sm3 $\xleftrightarrow{80° C.}$ SmC* $\xleftrightarrow{128.3° C.}$ SmA $\xleftrightarrow{171.0° C.}$ Ch $\xleftrightarrow{174.2° C.}$ Iso.

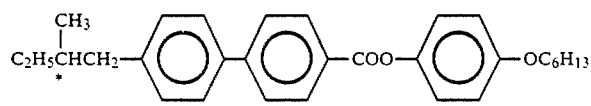

4-hexyloxyphenyl-4-(2''-methylbutyl)biphenyl-4'-carboxylate

Cryst. $\xrightleftharpoons{68.8°\ C.}$ SmC* $\xrightleftharpoons{80.2°\ C.}$ Ch. $\xrightleftharpoons{163.5°\ C.}$ Iso.

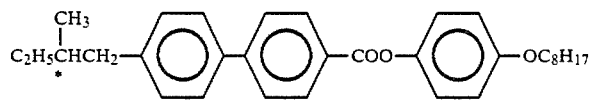

4-octyloxyphenyl-4-(2''-methylbutyl)biphenyl-4'-carboxylate

Cryst. $\xrightleftharpoons{76°\ C.}$ SmC* $\xrightleftharpoons{88.6°\ C.}$ Ch. $\xrightleftharpoons{155.4°\ C.}$ Iso.

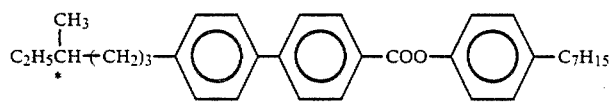

4-heptylphenyl-4-(2''-methylbutyl)biphenyl-4'-carboxylate

Cryst. $\xrightleftharpoons{91.5°\ C.}$ SmC* $\xrightleftharpoons{93°\ C.}$ SmA $\xrightleftharpoons{112°\ C.}$ Ch. $\xrightleftharpoons{131°\ C.}$ Iso.

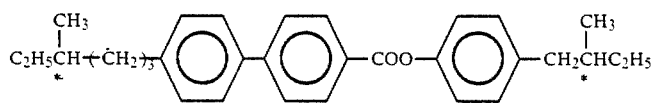

4-(2''-methylbutyl)phenyl-4-(4''-methylhexyl)biphenyl-4'-carboxylate

Cryst. $\xrightarrow{83.4°\ C.}$ Ch. $\xrightarrow{114°\ C.}$ Iso.
$\downarrow 81.0°\ C.$
SmC* $\xleftarrow{74.3°\ C.}$ SmA In addition to the above, the following mesomorphic compounds may suitably be combined with the trifluoroalkane derivative of the formula (I):

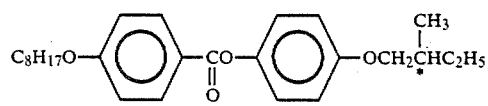

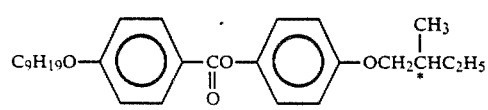

[third compound with C$_{10}$H$_{21}$O—⌬—CS—⌬—OCH$_2$CHC$_2$H$_5$ with CH$_3$]

Herein, the symbols used for describing phase-transition respectively denote the following phases.

(10)

(11)

(12)

(13)

| | |
|---|---|
| Cryst.: | crystal phase, |
| SmA: | smectic A phase, |
| SmC*: | chiral smectic phase, |
| N: | nematic phase, |
| Ch.: | cholesteric phase, |
| Iso.: | isotropic phase, |
| SmA: | smectic A phase, |
| SmB: | smectic B phase, and |
| Sm3: | smectic phase (un-identified) other than SmA and SmC*. |

The trifluoroalkane derivative represented by the formula (I) may also be mixed with a smectic liquid crystal such as those of the formulas (1)–(5) below which per se are not chiral to provide a composition which may be used as a ferroelectric liquid crystal. In this case, the trifluoroalkane derivative represented by the formula (I) may preferably be used in an amount of 0.1–99 wt. %, particularly 1–90 wt. %. The resultant composition may be provided with an increased spontaneous polarization corresponding to the content of a fluoroalkane derivative according to the present invention.

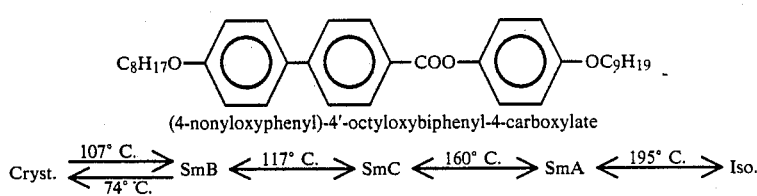
(4-nonyloxyphenyl)-4'-octyloxybiphenyl-4-carboxylate

Cryst. $\underset{74° C.}{\overset{107° C.}{\rightleftarrows}}$ SmB $\overset{117° C.}{\rightleftarrows}$ SmC $\overset{160° C.}{\rightleftarrows}$ SmA $\overset{195° C.}{\rightleftarrows}$ Iso.

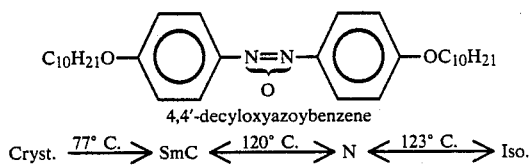
4,4'-decyloxyazoybenzene

Cryst. $\overset{77° C.}{\rightleftarrows}$ SmC $\overset{120° C.}{\rightleftarrows}$ N $\overset{123° C.}{\rightleftarrows}$ Iso.

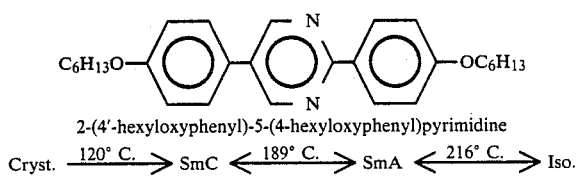
2-(4'-hexyloxyphenyl)-5-(4-hexyloxyphenyl)pyrimidine

Cryst. $\overset{120° C.}{\rightleftarrows}$ SmC $\overset{189° C.}{\rightleftarrows}$ SmA $\overset{216° C.}{\rightleftarrows}$ Iso.

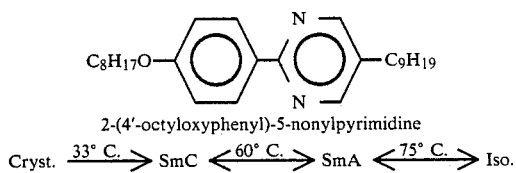
2-(4'-octyloxyphenyl)-5-nonylpyrimidine

Cryst. $\overset{33° C.}{\rightleftarrows}$ SmC $\overset{60° C.}{\rightleftarrows}$ SmA $\overset{75° C.}{\rightleftarrows}$ Iso.

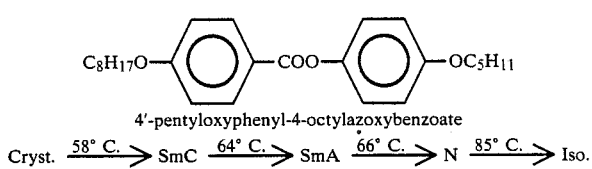
4'-pentyloxyphenyl-4-octylazoxybenzoate

Cryst. $\overset{58° C.}{\rightarrow}$ SmC $\overset{64° C.}{\rightarrow}$ SmA $\overset{66° C.}{\rightarrow}$ N $\overset{85° C.}{\rightarrow}$ Iso.

In addition to the above compounds of the formulas (1)–(5), compounds having a phenylpyrimidine skeleton or phenylbenzoate skeleton such as those of the following formulas ①–⑨ may suitably be used.

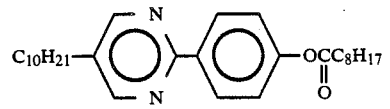  ①

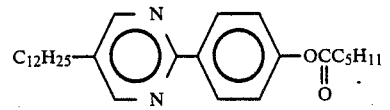  ②

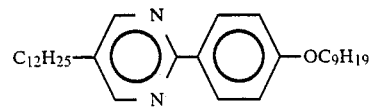  ③

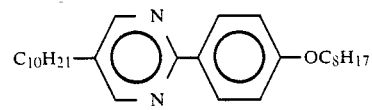  ④

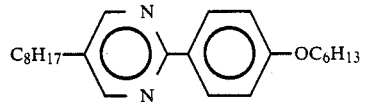  ⑤

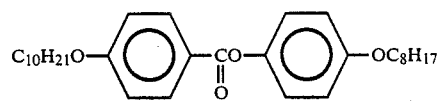  ⑥

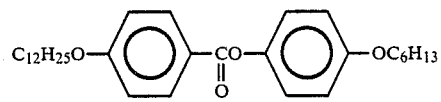  ⑦

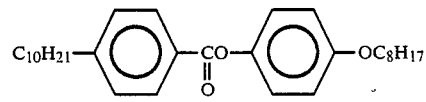  ⑧

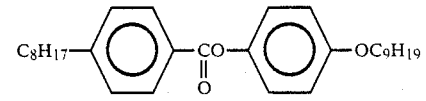  ⑨

Further, the trifluoroalkane derivative represented by the formula (I) may be added to a nematic liquid crystal to effectively prevent the occurrence of reverse domain in a TN-type cell. In this case, the trifluoroalkane derivative may be added in a proportion of 0.01–50 wt. % of the liquid crystal composition.

Further, the trifluoroalkane derivative may be added to a nematic liquid crystal or chiral nematic liquid crystal to provide a liquid crystal composition for use in a phase transition-type liquid crystal device or a guest-host liquid crystal device of the White-Taylor type. In this case, the trifluoroalkane derivative of the formula (I) may be used in a proportion of 0.01–80 wt. % of the resultant liquid crystal composition.

Hereinbelow, the present invention will be explained more specifically with reference to Experimental Examples.

EXAMPLE 1

Production of 3-trifluoromethylheptyl 4-[4-octyloxyphenyl]benzoate (Example Compound (2)).

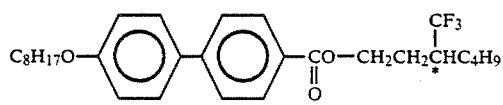

326 mg (1.00 mmol) of 4-[4-octyloxyphenyl]-benzoic acid and 3 ml of thionyl chloride were heat-refluxed for 2 hours. An excess of the thionyl chloride was distilled off, and 224 mg (2.0 mmol) of triethylenediamine, 4 ml of dry benzene and 221 mg (1.2 mmol) of (−)-3-trifluoromethyl-1-heptanol were added thereto, followed by 1 hour of reaction at 50° C., addition of 31 mg (1.3 mmol) of sodium hydride and 2 hours of heat refluxing. After the reaction, 1M-hydrochloric acid and water were added to the reaction mixture, and the mixture was subjected to extraction with benzene and drying with anhydrous sodium sulfate. After distilling off the solvent, the product was purified by silica gel thin layer chromatography to obtain 260 mg of the above-captioned compound. Yield: 53%. Optical rotation $[\alpha]_D^{18}$ +8.1° (c 1, CH$_2$Cl$_2$).

EXAMPLE 2

Production of 4-(3-trifluoromethylheptyloxy)-phenyl 4-decyloxybenzoate (Example Compound (10)).

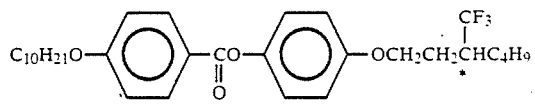

500 mg (2.62 mmol) of p-toluenesulfonyl chloride was added to a mixture of 480 mg (2.6 mmol) of (+)-3-trifluoromethyl-1-heptanol and 790 mg (10 mmol) of pyridine, and the resultant mixture was stirred for 2 hours at room temperature. After the reaction, the mixture was neutralized with 2M-hydrochloric acid and extracted with methylene chloride to obtain 820 mg of 3-trifluoromethylheptyl tosylate from the resultant methylene chloride layer. $[\alpha]_D^{23}$ +0.5° (c 2, CH$_2$Cl$_2$), $[\alpha]_{435}^{23}$ +2.2° (c 2, CH$_2$Cl$_2$), To a mixture of 390 mg (1.15 mmol) of the above tosylate, 250 mg (2.77 mmol) of hydroquinone and 3 ml of 1-butanol, 70 mg (1.75 mmol) of sodium hydroxide was added, followed by 5 hours of heating at 130° C. under stirring. After the reaction, water and 1M-hydrochloric acid was added, and the mixture was extracted with ether, followed by drying with anhydrous sodium sulfate. After distilling off the ether, the residue was purified by thin layer chromatography to obtain 170 mg of 4-(3-trifluoromethylheptyloxy)phenol. Yield: 54%. $[\alpha]_D^{26}$ −2.8° (c 1, CH$_2$Cl$_2$), $[\alpha]_{435}^{26}$ −4.9° (c 1, CH$_2$Cl$_2$).

On the other hand, 170 mg (0.61 mmol) of 4-decyloxybenzoic acid and 2 ml of thionyl chloride were heat-refluxed for 2 hours. Excessive thionyl chloride was distilled off, 170 mg (0.62 mmol) of the above-obtained 4-substituted phenol, 130 mg (1.2 mmol) of triethylenediamine and 2 ml of benzene were added, followed by heating at 50° C. for 1 hour, addition of 24 mg of sodium hydride and 2 hours of heat-refluxing. After the reaction, 1M-hydrochloric acid and water were added, followed by extraction with benzene. After distilling off the solvent, the product was purified by silica gel column chomatography (solvent: benzene) to obtain 260 mg of 4-(3-trifluoromethylheptyloxy)phenol 4-decyloxybenzoate. Yield 79%. $[\alpha]_D^{26}$ −2.8° (c 1, CH$_2$Cl$_2$).

EXAMPLE 3

Production of 4-(3-trifluoromethylheptyloxy)-phenyl 4′-[4″-octyloxyphenyl]benzoate (Example Compound (15)).

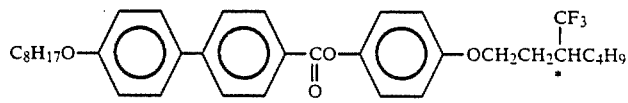

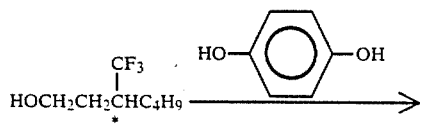

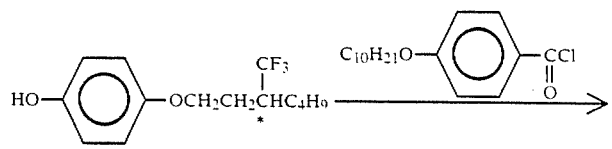

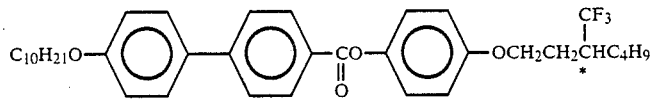

-continued

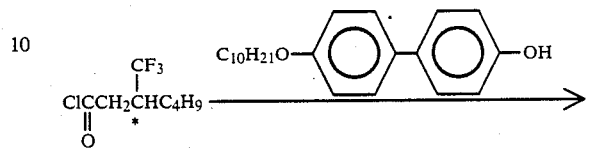

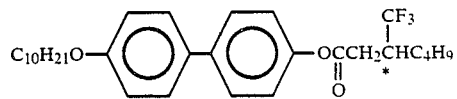

By repeating steps similarly as in Example 2, the above objective compound was synthesized from 4-(3-trifluoromethylheptyloxy)phenol and 4-[4-octyloxyphenyl]benzoic acid. $[\alpha]_D^{24}$ −2.9° (c 1, $CH_2Cl_2$),

EXAMPLE 4

Production of 4-(5-decyl-2-pyrimidyl)phenyl 3-trifluoromethylheptanoate (Example Compound (29)).

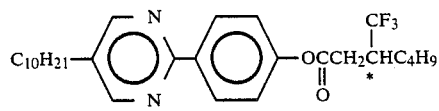

300 mg (1.5 mmol) of (+)-3-trifluoromethylheptanoic acid and 3 ml of thionyl chloride were heat-refluxed for 2 hours. After distilling off an excess of the thionyl chloride, 336 mg (3 mmol) of triethylenediamine and 470 mg (1.5 mmol) of 4-(5-decyl-2-pyrimidyl)phenol were added, followed by 1 hour of heating at 50° C., addition of 40 mg of sodium hydride and 2 hours of heat refluxing. Thereafter, the post treatments were conducted similarly as in Example 2, followed by purification by silica gel column chromatography (solvent: methylene chloride) to obtain 490 mg of the above-captioned compound. Yield 66%. $[\alpha]_D^{22}$ +6.1° (c 2, $CH_2Cl_2$),

EXAMPLE 5

Production of 4-(4-decyloxyphenyl)phenyl 3-trifluoromethyl-heptanoate (Example Compound (31))

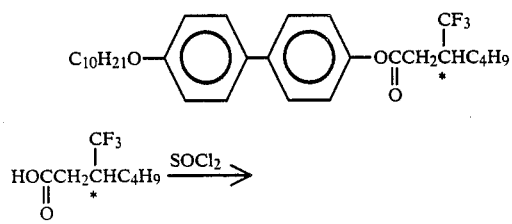

By repeating similar steps as in Example 4, the above-captioned compound was synthesized from 3-trifluoromethy-heptanoic acid and 4'-decyloxy-4-hydroxybiphenyl. $[\alpha]_D^{24}$ +6.0° (c 1, $CH_2Cl_2$),

EXAMPLE 6

2-[4-(3-trifluoromethylheptyloxy)phenyl]-5-decylpyrimidine (Example Compound (25)),

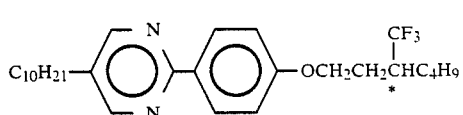

The above compound was synthesized from 3-trifluoromethylheptyl tosylate and 4-(5-decyl-2-pyrimidyl)phenol through similar steps as in Example 2. $[\alpha]_D^{25}$ −3.0° (c 1, $CH_2Cl_2$),

EXAMPLE 7

4-(3-trifluoromethylheptyloxy)phenyl 4-[4-dodecyloxyphenyl]benzoate (Example Compound (18)),

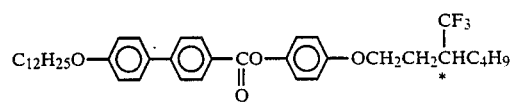

The above compound was synthesized from 4-(3-trifluoromethylheptyloxy)phenol and 4-[4-dodecyloxyphenyl]benzoic acid through similar steps as in Example 2.

The mesomorphic compounds obtain by Examples 1–7 in the above-described manner are inclusively listed in the following Table 1 together with their optical rotation and phase transition characteristic.

In the following table and hereinafter, Cryst. denotes crystalline state; Iso. isotropic liquid; Ch, cholesteric phase; $S_A$, smectic A phase; $S_C^*$, chiral smectic C phase; and $S_3$, $S_4$, unidentified smectic phases.

TABLE 1

| Example | Structural formula | Optical rotation (conc. solvent) | Phase transition temperature (°C.) |
|---|---|---|---|
| 1 | C$_8$H$_{17}$—⌬—⌬—COCH$_2$CH$_2$*CHC$_4$H$_9$ with CF$_3$, O | $[\alpha]_D^{24}$ +8.1 (c1, CH$_2$Cl$_2$) | Cryst. $\underset{30}{\overset{42}{\rightleftarrows}}$ Iso., Iso. $\xrightarrow{35}$ S$_A$ |
| 2 | C$_8$H$_{17}$O—⌬—⌬—CO—O—⌬—OCH$_2$CH$_2$*CHC$_4$H$_9$ (CF$_3$) | $[\alpha]_D^{24}$ −2.9 (c1, CH$_2$Cl$_2$) | S$_A$ $\underset{40}{\overset{}{\rightleftarrows}}$ Cryst. $\underset{35}{\overset{}{\rightleftarrows}}$ S$_3$ $\underset{84}{\overset{85}{\rightleftarrows}}$ S$_C$* $\underset{116}{\overset{117}{\rightleftarrows}}$ S$_A$ $\underset{164}{\overset{165}{\rightleftarrows}}$ Iso. ; S$_4$ $\xrightarrow{68}$ ; $\xrightarrow{40}$ |
| 3 | C$_{10}$H$_{21}$O—⌬—CO—O—⌬—OCH$_2$CH$_2$*CHC$_4$H$_9$ (CF$_3$) | $[\alpha]_D^{26}$ −2.8 (c1, CH$_2$Cl$_2$) | Cryst. $\underset{-5}{\overset{40}{\rightleftarrows}}$ Iso., Iso. $\underset{12}{\overset{33}{\rightleftarrows}}$ S$_3$, S$_3$ $\rightarrow$ S$_A$ |
| 4 | C$_{10}$H$_{21}$—⌬(N,N pyrimidine)—⌬—OCCH$_2$*CHC$_4$H$_9$ (CF$_3$), O | $[\alpha]_D^{22}$ +6.1 (c2, CH$_2$Cl$_2$) | Cryst. $\underset{-4}{\overset{28}{\rightleftarrows}}$ Iso., S$_4$ $\underset{1}{\overset{-7}{\rightleftarrows}}$ S$_3$ |
| 5 | C$_{10}$H$_{21}$O—⌬—⌬—OCCH$_2$*CHC$_4$H$_9$ (CF$_3$), O | $[\alpha]_D^{24}$ +6.0 (c1, CH$_2$Cl$_2$) | Cryst. $\underset{50}{\overset{58}{\rightleftarrows}}$ Iso. |
| 6 | C$_{10}$H$_{21}$—⌬(N,N pyrimidine)—⌬—OCH$_2$CH$_2$*CHC$_4$H$_9$ (CF$_3$) | $[\alpha]_D^{25}$ −3.0 (c1, CH$_2$Cl$_2$) | Cryst. $\underset{14}{\overset{38}{\rightleftarrows}}$ Iso. |
| 7 | C$_{12}$H$_{25}$O—⌬—⌬—CO—O—⌬—OCH$_2$CH$_2$*CHC$_4$H$_9$ (CF$_3$) | | S$_C$* $\underset{119}{\overset{120}{\rightleftarrows}}$ S$_A$ $\underset{145}{\overset{146}{\rightleftarrows}}$ Iso. ; Cryst. $\overset{58}{\rightarrow}$ S$_3$ $\xrightarrow{40}$ ; $\xrightarrow{36}$ Cryst. |

EXAMPLE 8

Optically active 4″-(4-trifluoromethyloctyloxy)phenyl 4-decyloxybiphenyl-4′-carboxylate (Example Compound (19)) was produced along the following reaction scheme including the steps as described hereinafter.

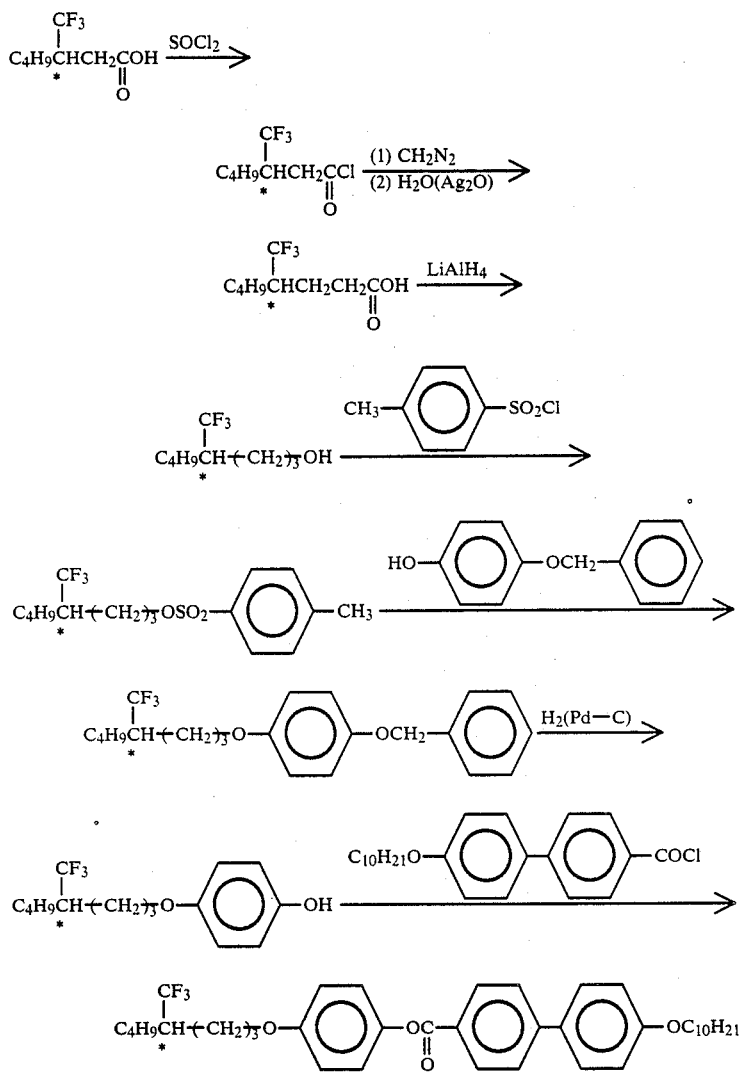

(Step 1)

Production of 4-trifluoromethyloctanoic acid 2.0 g (10 mmol) of 3-trifluoromethylheptanoic acid and 6 ml (about 80 mmol) of thionyl chloride were reacted for 2 hours under heat-refluxing, followed by distillation to obtain 1.8 g of 3-trifluoromethylheptanoic acid chloride (b.p.: 72.2°–75.0° C./25 mmHg). The acid chloride was dissolved in 10 ml of diethyl ether and added dropwise to a preliminarily ice-cooled ether solution of diazomethane, followed by stirring overnight at room temperature. After distilling off the solvent, the remainder was suspended in 15 ml of dioxane and then added to an aqueous solution at 70° C. of 1.1 g of silver oxide and 2.7 g of sodium thiosulfate (penta-hydrate), followed by stirring for 70 min. After the reaction, potassium hydroxide aqueous solution was added thereto and the mixture was filtered. 5N-nitric acid was added to the filtrate to provide an acidity as judged by Congo Red, followed by extraction with diethyl ether. The resultant ether layer was dried with anhydrous sodium sulfate, followed by distilling-off of the solvent and distillation of the product to obtain 0.42 g of objective 4-trifluoromethyloctanoic acid (b.p.: 130°–135° C./26 mmHg).

(Step 2)

Production of 4-trifluoromethyloctanol

In a flask replaced with nitrogen, 72 mg (1.9 mmol) of lithium aluminum hydride and 2 ml of dry diethyl ether were placed and cooled with ice, and a solution of 0.4 g (1.9 mmol) 4-trifluoromethyloctanoic acid in 1 ml of dry diethyl ether was added dropwise thereto. The mixture was stirred for 4 hours on an ice bath for reaction, and a saturated sulfate aqueous solution was added thereto, followed by decantation to recover the ether layer. The ether solution was dried on sodium sulfate, followed by distilling-off of the solvent and distillation for purification to obtain 0.27 g of 4-trifluoromethyloctanol. Yield: 71%, B.P.: 80°–85° C./19 mmHg.

(Step 3)

Production of
p-benzyloxy-(4-trifluoromethyloctyloxy)phenyl 0.27 g (1.4 mmol) of 4-trifluoromethyloctanol was dissolved in 5 ml of pyridine and cooled with ice, and 0.27 g (1.4 mmol) of p-toluenesulfonyl chloride was added thereto under stirring, followed by reaction at 15°–20° C. for 3 hours. After the reaction, the mixture was acidified with 2N-hydrochloric acid and extracted with diethyl ether. The resultant ether layer was dired on anhydrous sodium sulfate, followed by distilling-off of the solvent to obtain 4-trifluoromethyloctyl p-toluenesulfonate. Then, 0.4 g (1.1 mmol) of the 4-trifluoromethyloctyl p-toluenesulfonate was dissolved in 1 ml of ethanol and then added to a preliminarily prepared solution of 48 mg (1.1 mmol) of sodium hydroxide and 0.23 g (1.1 mmol) of p-hydroxyphenyl benzyl ether in 1 ml of ethanol. The mixture was heated to 85°–90° C. for 5 hours of reaction and then cooled by standing. The reaction mixture was poured into 20 ml of 2N-hydrochloric acid and extracted with diethyl ether. The resultant ether layer was dried on anhydrous sodium sulfate and purified by silica gel column chromatography (eluent: benzene) to obtain 0.30 g (yield: 69%) of p-benzyloxy(4-trifluoromethyloctyloxy)phenyl.
(Step 4)

Production of (4-trifluoromethyloctyloxy)phenol 0.29 g (0.78 mmol) of p-benzyloxy(4-trifluoromethyloctyloxy)phenyl, 35 mg of 5% palladium-activated carbon and 3 ml of ethanol were placed in a flask and subjected to catalytic hydrogenation to obtain 0.22 g of p-(4-trifluoromethyloctyloxy)phenol. Yield: 97%.
(Step 5)

Production of 4″-(4-trifluoromethyloctyloxy)phenyl 4-decyloxybiphenyl-4′-carboxylate 0.27 g of 4-decyloxybiphenyl-4′-carboxylate and 2 ml of thionyl chloride were heat-refluxed for 2 hours to form an acidchloride. Separately, 0.22 g of p-(4-trifluoromethyloctyloxy)phenol and 0.17 g of triethylenediamine were dissolved in 2 ml of benzene, and a solution of the acidchloride in 3 ml of benzene was added thereto dropwise. The mixture was stirred for 2 hours at 50° C., and 44 mg of sodium hydride (60%), followed by 2 hours of reaction at 90° C. After the reaction, the mixture was poured into iced water, acidified with hydrochloric acid and extracted with diethyl ether. The resultant ether layer was washed with saturated saline water, dried with anhydrous sodium sulfate and subjected to drying-off of the solvent. The crude product was purified by silica gel column chromatography (eluent: benzene/hexane=1/1) and recrystallized from petroleum ether to obtain 0.34 g of optically active 4″-(4-trifluoromethyloctyloxy)phenyl 4-decyloxybiphenyl-4′-carboxylate. Yield: 71%.

EXAMPLE 9

Optically active 4′-octyloxycarbonyloxybiphenyl-4-(3-trifluoromethylheptanoate) (Example Compound (20)) was produced along the following reaction scheme.

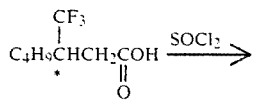

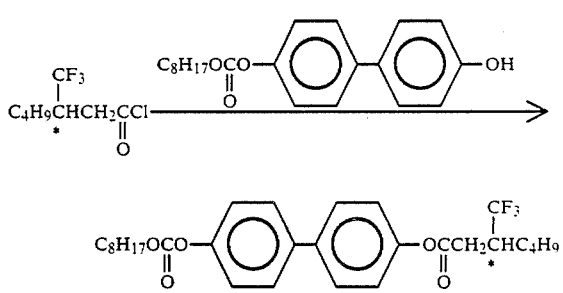

0.20 g (1 mmol) of 3-trifluoromethylheptanoic acid and 2 ml of thionyl chloride were reacted under heat-refluxing to form an acid chloride, which was, after removal of excessive thionyl chloride by distillation, dissolved in 2 ml of benzene. Separately, 0.22 mg (2 mmol) of triethylenediamine and 0.34 g (1 mmol) of 4-octyloxycarbonyloxy-4′-biphenol were dissolved in 1 ml of benzene, and the above-prepared benzene solution of the acid chloride was added dropwise thereto, followed by 2 hours of reaction at 50° C. To the reaction mixture was further added 60 mg (1.5 mmol) of sodium hydride (60%), followed by reaction for 30 min at 90° C. and overnight at room temperature. After the reaction, the reaction mixture was poured into water, acidified with hydrochloric acid and extracted with diethyl ether. The resultant ether layer was dried with anhydrous sodium sulfate and subjected to distilling-off of the solvent and purification by silica gel column chromatography (eluent: ethyl acetate/hexane=2/9) to obtain 0.25 g of objective optically active 4′-octyloxycarbonyloxybiphenyl 4-(3-trifluoromethylheptanoate). Yield: 48%. $[\alpha]_D^{30}$ +4.5, $[\alpha]_{435}^{27}$ +11.9 (c 1.09, chloroform).

EXAMPLE 10

Optically active 4′-(4″-propylcyclohexylcarbonyloxy)biphenyl-4-(3-trifluoromethylheptanoate) (Example Compound (21)) was prepared along the following reaction scheme.

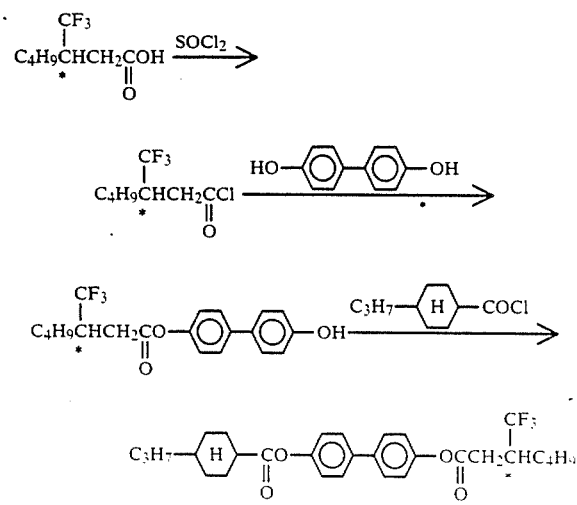

(Step 1)

Production of
4-(3-trifluoromethylhexylcarbonyloxy)-4'-biphenol 2.10 g (10.6 mmol) of 3-trifluoromethylheptanoic acid and 3 ml of thionyl chloride were heat-refluxed under stirring for 1 hour, followed by distilling-off of excessive thionyl chloride and dissolution in 5 ml of toluene. In a separate vessel, 4.6 g (25 mmol) of bisphenol, 40 ml of pyridine and 10 ml of benzene were placed and stirred, and the above-prepared toluene solution of 3-trifluoromethylheptanoic chloride was added dropwise thereto. After reaction for 2 hours at 50° C. and further for 2 hours at 90° C., the reaction mixture was poured into 100 ml of iced water and extracted with diethyl ether. The resultant ether layer was washed with 5%-saline water, followed by drying with anhydrous sodium sulfate, distilling-off of the solvent and purification by recrystallization to obtain 2.9 g of 4-(3-trifluoromethylhexylcarbonyloxy)-4'-biphenol. Yield: 40%.

(Step 2)

Production of
4'-(4''-propylcyclohexylcarbonyloxy)biphenyl-4-(3-trifluoromethylheptanoate)

A solution of 85 mg (0.76 mmol) of triethylenediamine in 2 ml of dry benzene was added to 0.14 g (0.38 mmol) of 4-(3-trifluoromethylhexylcarbonyloxy)biphenol, followed by stirring. Further, a solution of 70 mg (0.38 mmol) of 4-n-propylcyclohexylcarboxylic acid chloride in 0.5 ml of dry benzene was added thereto dropwise, followed by 2 hours of reaction at 50° C. Then, 30 mg (0.76 mmol) of sodium hydride (60%) was added thereto, followed by 2 hours of heat-refluxing. After the reaction, the reaction mixture was cooled by standing, acidified with 1N-hydrochloric acid and extracted with diethyl ether. The resultant ether layer was washed with 5%-saline water, dried with anhydrous sodium sulfate and subjected to distilling-off of the solvent and purification by silica gel column chromatography (eluent: benzene) to obtain 0.18 g of objective optically active 4'-(4''-propylcyclohexylcarbonyloxy)-biphenyl-4-(3-trifluoromethylheptanoate). Yield: 90%.

The phase transition characteristics of the mesomorphic compounds obtained in Examples 8–10 are respectively shown in the following Table 2.

TABLE 2

| Example | Structural formula | Phase transition temperature (°C.) |
|---|---|---|
| 8 | C₁₀H₂₁O—⌬—⌬—CO—O—⌬—O(CH₂)₂CHC₄H₉ with CF₃ branch, * | Cryst. ⇌(35/0) S₃ ⇌(55/54) Sc* ⇌(118/118) S₁ ⇌(154/152) Iso. |
| 9 | C₈H₁₇OCO—⌬—⌬—O—⌬—OCCH₂CHC₄H₉ with CF₃ branch, O=, * | Cryst. → Iso. 25.0 ↓ 0.7 ↓ S₄ ←(5.0) S₃ |
| 10 | C₃H₇—(H)—CO—O—⌬—⌬—OCCH₂CHC₄H₉ with CF₃ branch, O=, * | Cryst. ⇌(62/58) S₃ ⇌(110/109) S₁ ⇌(143/142) Iso. |

EXAMPLE 11

4-octyl-4'-[4''-(3'''-trifluoromethylheptyloxy)benzyloxy]biphenyl (Example Compound (41)) was prepared along the following reaction scheme.

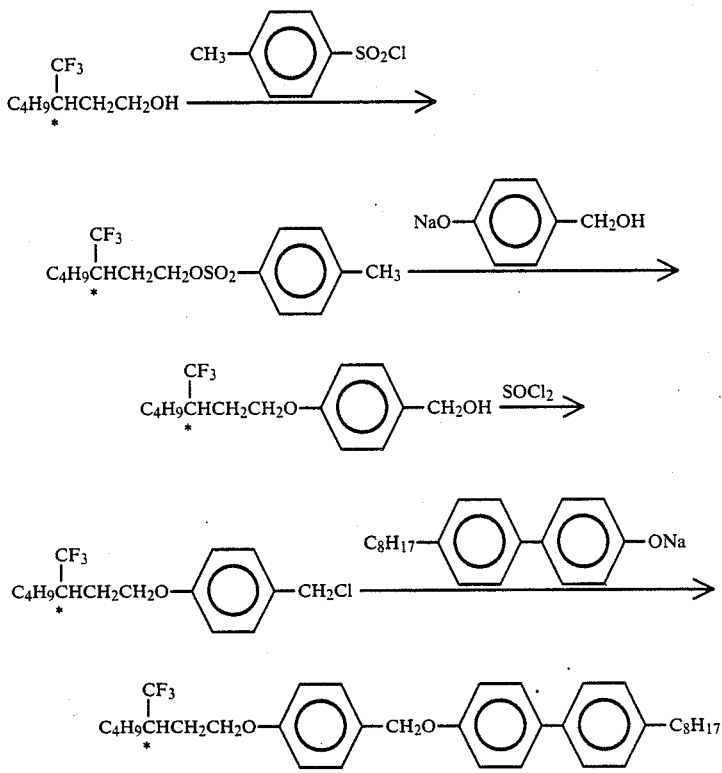

(Step 1)

Production of (+)-3-trifluoromethylheptyl p-toluenesulfonate

In a round-bottomed flask, 3.3 g of (−)-3-trifluoromethyl-1-heptanol and 5.7 g of pyridine were placed and stirred, and 3.4 g of p-toluenesulfonyl chloride was added, followed by 4 hours of reaction at 15°–20° C. The reaction mixture was poured into water, acidified with hydrochloric acid and extracted with diethyl ether, followed further by drying with sodium sulfate, and distilling-off of the solvent to obtain 5.3 g of (+)-3-trifluoromethylheptyl p-toluenesulfonate.

(Step 2)

Production of (+)-p-(3-trifluoromethylheptyloxy)benzyl alcohol

In a round-bottomed flask, a solution of 2.4 g of p-hydroxybenzyl alcohol in 10 ml of ethanol and 5.3 g of (+)-3-trifluoromethylheptyl p-toluenesulfonate were placed, and a solution of 0.8 g of sodium hydroxide in 10 ml of ethanol was added thereto dropwise, followed by 6 hours of heat-refluxing, cooling by standing and acidification with hydrochloric acid. The organic layer was extracted with diethyl ether. The resultant ether solution was dried with sodium sulfate and subjected to distilling-off of the solvent and purification by silica gel column chromatography to obtain 4.4 g of (+)-p-(3-trifluoromethylheptyloxy)benzyl alcohol. $[\alpha]_D^{28}$ +1.0°, $[\alpha]_{435}^{27}$ +2.4° (c 5.0, chloroform).

(Step 3)

Production of 4-octyl-4'-[4''-(3'''-trifluoromethylheptyloxy)benzyloxy]biphenyl 0.58 g of (+)-p-(3-trifluoromethylheptyloxy)benzyl alcohol and 1.5 ml of thionyl chloride were heat-refluxed for 5 hours, and excessive thionyl chloride was distilled off to obtain an acid chloride. Separately, 0.62 g of p-octylbiphenol was dissolved in 7 ml of THF and reacted with sodium hydride to form a sodium salt, and to the solution, a solution of the above-prepared acid chloride in 2 ml of dimethyl sulfoxide was added dropwise, followed by 4 hours of heat-refluxing. After the reaction, the reaction mixture was poured into water, acidified with hydrochloric acid and extracted with diethyl ether. The ether solution was dried with sodium sulfate and subjected to distilling-off of the solvent and purification by silica gel column chromatography to obtain 0.5 g of the objective compound. $[\alpha]_{435}^{34}$ +3.6 (c 0.5, $CHCl_3$).

EXAMPLE 12

5-dodecyl-2-{4'-[4''-(3'''-trifluoromethylheptyloxy)benzyloxy]phenyl}pyrimidine (Example Compound (43)) was prepared along the following reaction scheme.

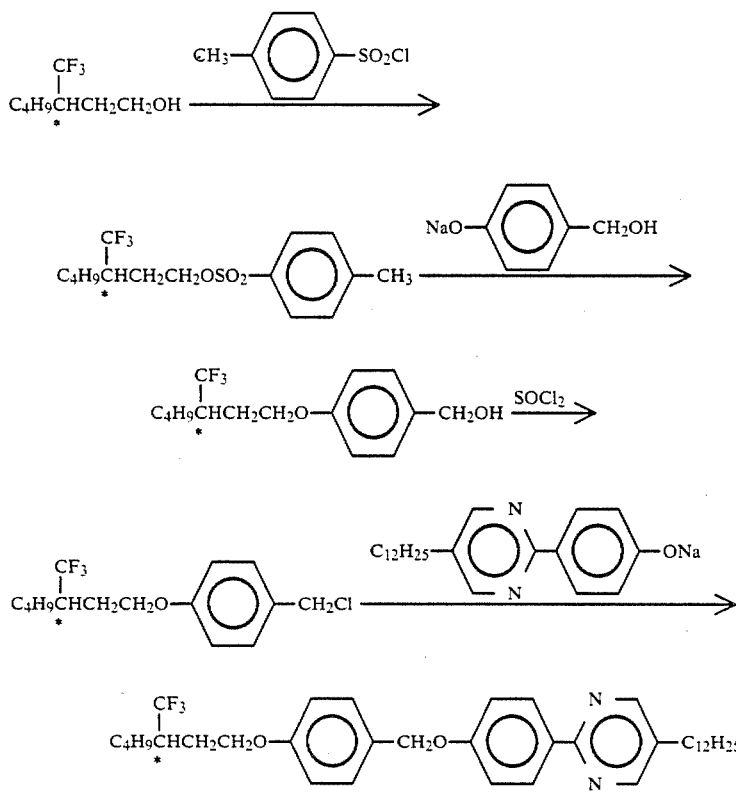

0.58 g of (+)-p-(3-trifluoromethylheptyloxy)benzyl alcohol prepared in a similar manner as in Steps (1) and (2) in Example 11 and 1.5 ml of thionyl chloride were heat-refluxed for 5 hours, followed by distilling-off of excessive thionyl chloride to obtain an acid chloride. Separately, 0.68 g of 5-dodecyl-2-(p-hydroxyphenyl)-pyrimidine was dissolved in 7 ml of THF and reacted with sodium hydride to form a sodium salt, and to the solution, a solution of the above-prepared acid chloride in 2 ml of dimethyl sulfoxide was added dropwise, followed by 4 hours of heat-refluxing. After the reaction, the reaction mixture was poured into water, acidified with hydrochloric acid and extracted with diethyl ether. The ether solution was dried with sodium sulfate and subjected to distilling-off of the solvent and purification by silica gel column chromatography to obtain 0.17 g of the objective compound. $[\alpha]_{435}^{29}$ +4.7 (c 1, $CHCl_3$).

EXAMPLE 13

P'-octylbiphenyl p-(3-trifluoromethylheptyloxy)benzoate (Example Compound (70)) was prepared along the following reaction scheme.

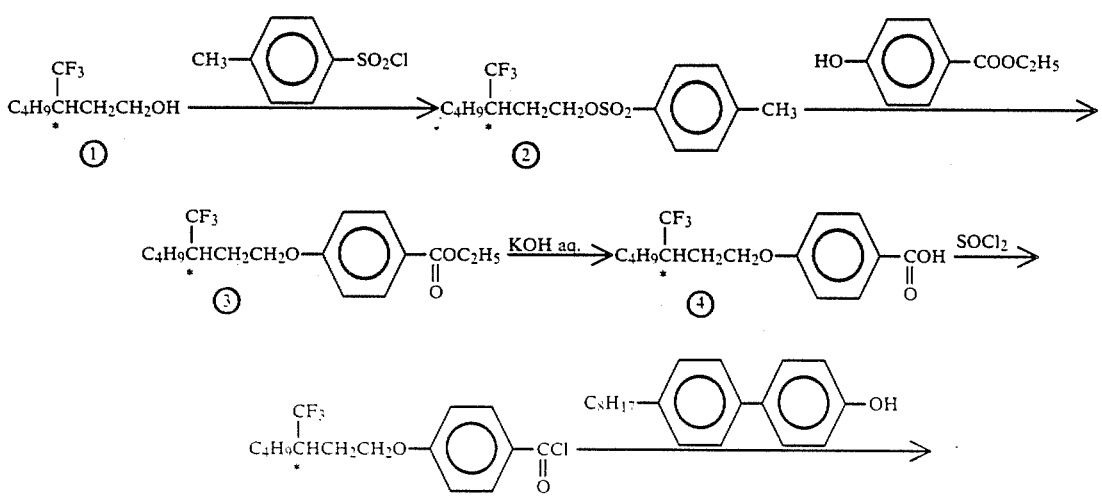

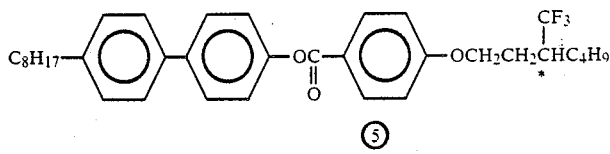

(Step 1)

Production of 3-trifluoromethylheptyl p-toluenesulfonate ②

In a round bottomed flask, 1.3 g of optically active 3-trifluoromethyl-1-heptanol and 2.3 g of pyridine were placed and cooled with ice, and 1.4 g of p-toluenesulfonyl chloride was added, followed by 4 hours of stirring at 20° C. After the reaction, dilute hydrochloric acid was added, and the mixture was subjected to two times of extraction with diethyl ether. The resultant ether layer was neutralized by washing with water, dried with magnesium sulfate and purified by silica gel column chromatography (developer: hexane/diethyl ether=2/1) to obtain 2.1 g of 3-trifluoromethylheptyl p-toluenesulfonate ②. (Yield: 88%).

(Step 2)

Production of p-(3-trifluoromethylheptyloxy)benzoic acid ④

In a round-bottomed flask, 0.88 g of the 3-trifluoromethylheptyl p-toluenesulfonate ②, 0.4 g of ethyl p-hydroxybenzoate and 1 ml of dimethylformamide were placed, and 50 mg of sodium hydride was added thereto, followed by 8 hours of heat-refluxing and 15 hours of standing at room temperature. After the reaction, dimethylformamide was distilled off, and dilute hydrochloric acid was added to the product, which was then extracted with methylene chloride. The resultant organic layer was washed with water and dried with magnesium sulfate, followed by distilling-off of the solvent and purification by thin layer chromatography (developer: methylene chloride/hexane=1/1) to obtain 0.7 g of ethyl p-(3-trifluoromethylheptyloxy)benzoate ③. (Yield: 80%).

In a round-bottomed flask, 0.27 g of sodium hydroxide and 1 ml of water were placed, 3 ml of methanol was added and then 0.7 g of ethyl p-(3-trifluoromethylheptyloxy)benzoate was added thereto, followed by 4 hours of reaction at 50° C. Then, water was added to the system, and methanol was distilled off, followed by addition of 6N-hydrochloric acid to recover a precipitated crystal. The crystal was dried in a desiccator to obtain 0.55 g of p-(3-trifluoromethylheptyloxy)benzoic acid ④. (Yield: 90%).

IR date (cm$^{-1}$) 3420, 2940, 1660, 1600, 1420, 1240, 1160, 840, 760, 640.

Further, two enanthiomers of the acid ④ obtained by using two enanthiomers of the starting alcohol ① gave the following optical rotation data when measured in chloroform.

| Starting alcohol ① | Optical rotation [α]$_D$ | |
|---|---|---|
| | ① | ④ |
| (−)-enanthiomer | −2.3° (c1) | +4.2° (c1) |
| (+)-enanthiomer | +1.8° (c1) | −3.5° (c2) |

(Step 3)

Production of p'-octyloxybiphenyl p-(3-trifluoromethylheptyloxybenzoate) ⑤

0.2 g of p-(3-trifluoromethylheptyloxy)benzoic acid and 2 ml of thionyl chloride were heat-refluxed for 2 hours, followed by distilling-off of excessive thionyl chloride. Then, 0.16 g of triethylenediamine, 0.24 g of p-octylbiphenol and 1 ml of dry benzene were added thereto, followed by 1 hour of reaction at 50° C. Then, 19 mg of sodium hydride was added, and the mixture was heat-refluxed for 2 hours for reaction, followed by addition of dilute hydrochloric acid and extraction with benzene. The resultant organic layer was washed with water, dried with sodium sulfate and purified by TLC (thin layer chromatography) (developer: benzene), followed by recrystallization from ethanol to obtain 0.25 g of p'-octylbiphenyl p-(3-trifluoromethylheptyloxy)benzoate (Yield: 66%).

EXAMPLES 14–17

Mesomorphic ester compounds shown in Table 3 were obtained by repeating the steps of Example 13 and replacing the p-octylbiphenol with other p-substituted phenols shown in Table 3.

TABLE 3

Summary of synthesis examples of mesomorphic compounds

| Example | p-substituted phenol | Ester compounds | Yield |
|---|---|---|---|
| 14 |  |  | 39 |
| 15 |  |  | 69 |

TABLE 3-continued
Summary of synthesis examples of mesomorphic compounds

| Example | p-substituted phenol | Ester compounds | Yield |
|---|---|---|---|
| 16 | C₁₂H₂₅—[pyrimidine]—[phenyl]—OH | C₁₂H₂₅—[pyrimidine]—[phenyl]—OC(=O)—[phenyl]—OCH₂CH₂C*H(CF₃)C₄H₉  ⑧ | 21 |
| 17 | C₈H₁₇—[cyclohexyl]—[phenyl]—OH | C₈H₁₇—[cyclohexyl]—[phenyl]—OC(=O)—[phenyl]—OCH₂CH₂C*H(CF₃)C₄H₉  ⑨ | 24 |

The phase transition characteristics of the mesomorphic compounds ⑤–⑨ obtained in Examples 13–17 are given in the following Table 4.

TABLE 4

Phase transition temperatures of mesomorphic compounds ⑤–⑨

| Example | Structural formula | Phase transition temperature (°C.) |
|---|---|---|
| 13 | C$_8$H$_{17}$–〇–〇–〇–OC(=O)–〇–OCH$_2$CH$_2$CHC$_4$H$_9$ (with CF$_3$, *) ⑤ Example Compound (70) | Cry. $\xrightarrow{86}\xleftarrow{62}$ Sc* $\xrightarrow{91}\xleftarrow{90}$ Ch. $\xrightarrow{104}\xleftarrow{103}$ Iso. |
| 14 | C$_6$H$_{13}$OC(=O)–〇–〇–〇–OC(=O)–〇–OCH$_2$CH$_2$CHC$_4$H$_9$ (with CF$_3$, *) ⑥ Example Compound (72) | Cry. $\xrightarrow{53}$ Sc* $\xrightarrow{78}\xleftarrow{78}$ S$_A$ $\xrightarrow{101}\xleftarrow{101}$ Iso. |
| 15 | C$_{10}$H$_{21}$–〇(N,N)–〇–OC(=O)–〇–OCH$_2$CH$_2$CHC$_4$H$_9$ (with CF$_3$, *) ⑦ Example Compound (80) | Cry. $\xrightarrow{85}$ Ch. $\xrightarrow{95}$ Iso. $\xleftarrow{94}$  $\xleftarrow{67}$ Sc* $\xleftarrow{50}$ |
| 16 | C$_{12}$H$_{25}$–〇(N)–〇–OC(=O)–〇–OCH$_2$CH$_2$CHC$_4$H$_9$ (with CF$_3$, *) ⑧ Example Compound (77) | Cry. $\xrightarrow{46}\xleftarrow{27}$ S$_3$ $\xrightarrow{63}\xleftarrow{46}$ Sc* $\xrightarrow{75}\xleftarrow{74}$ Ch. $\xrightarrow{91}\xleftarrow{90}$ Iso. |
| 17 | C$_8$H$_{17}$–〈H〉–〇–OC(=O)–〇–OCH$_2$CH$_2$CHC$_4$H$_9$ (with CF$_3$, *) ⑨ Example Compound (78) | Cry. $\xrightarrow{65}$ Sc* $\xrightarrow{93}\xleftarrow{90}$ S$_A$ $\xrightarrow{108}\xleftarrow{107}$ Iso. $\xleftarrow{43}$ S$_3$ $\xleftarrow{29}$ |

EXAMPLE 18

Optically active p-decyloxybiphenyl p-(3-trifluoromethylnonyloxy)benzoate (Example Compound (93)) was prepared in the following manner.

146 mg (0.44 mmol) of (−)-p-(3-trifluoromethylnonyloxy)benzoic acid and 2.3 ml of thionyl chloride were heat-refluxed for 2 hours, followed by distilling-off of excessive thionyl chloride under reduced pressure. Then, addition of 1 ml of dry benzene and distilling-off under reduced pressure were repeated two times. To the system, a mixture of 99 mg (0.88 mmol) of triethylenediamine and 1 ml of dry benzene further dried with potassium hydride and 181 mg (0.55 mmol) of 4-decyloxy-4'-biphenol were added, followed by 1 hour of reaction at 50° C. Separately, 22 mg (0.55 mmol) of sodium hydride (60%) was washed with dry benzene to remove liquid paraffin and mixed with 0.5 ml of dry benzene. The mixture was then added to the above reaction system, followed by 2 hours of heat-refluxing. Then, 1N-hydrochloric acid was added until pH 2, 10 ml of water was added and extraction with benzene was effected. The resultant organic layer was dried with sodium sulfate and purified by TLC (developer: benzene/hexane=2/1). The product was further washed with hexane to obtain 64 mg of optically active p'-decyloxybiphenyl p-(3-trifluoromethylnonyloxy)benzoate. (Yield: 23%).

Phase transition temperature (°C.).

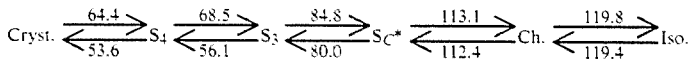

EXAMPLE 19

A liquid crystal composition A as shown below containing the mesomorphic compound of Example 3 as a component was prepared. For comparison, a liquid crystal composition M as shown below not containing the mesomorphic compound of Example 3 was also prepared. The phase transition temperatures and spontaneous polarization of the liquid crystal compositions A and M are given in Tables 5 and 6 appearing hereinafter.

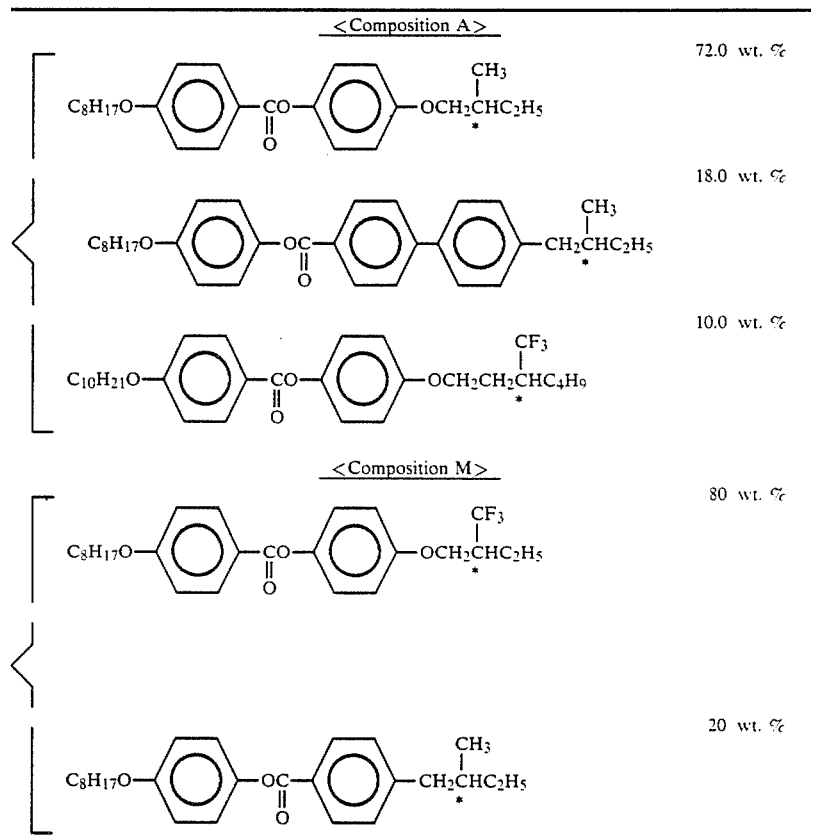

The above liquid crystal compositions A and M were evaluated in the following manner.

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K. K.) is isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 2%-solution of polyimide resin precursor (SP-510, available from Toray K. K.) in dimethylacetoamide by a spinner coater rotating at 2000 rpm for 15 seconds. Thereafter, the coating film was subjected to heat curing at 300° C. for 60 min. to obtain about 700 Å-thick film. The coating film was rubbed with acetate fiber-planted cloth. The thus treated two glass plates were washed with isopropyl alcohol. After alumina beads with an average particle size of 2.0 μm were dispersed on one of the glass plates, the two glass plates were applied to each other with a bonding sealing agent (Lixon Bond available from Chisso K. K.) so that their rubbed directions were parallel to each other and heated at 100° C. for 60 min. to form a blank cell. The cell gap was found to be about 2 μm as measured by a Berek compensator. Two cells were prepared in this way.

Then, each of the liquid crystal compositions A and M prepared above was heated into an isotropic liquid, and injected into a cell prepared above under vacuum and, after sealing, was gradually cooled at a rate of 0.5° C./hour to prepare two ferroelectric liquid crystal devices.

The ferroelectric liquid crystal devices were subjected to measurement of an optical response time (time from voltage application until the transmittance change reaches 90% of the maximum under the application of a peak-to-peak voltage Vpp of 30 V in combination with right-angle cross-nicol polarizers).

The results are shown in Table 7 appearing hereinafter.

EXAMPLES 20, 21

Liquid crystal compositions B and C as shown below were prepared by replacing the mesomorphic compound of Example 3 in the liquid crystal composition A in Example 19 with mesomorphic compounds prepared in Examples 4 and 6, respectively, in the same amount of 10 wt. % of the resultant composition. The phase transition temperatures, spontaneous polarization and optical response time of the liquid crystal compositions were measured and are also shown in Tables 5–7 appearing hereinafter.

<Composition B>

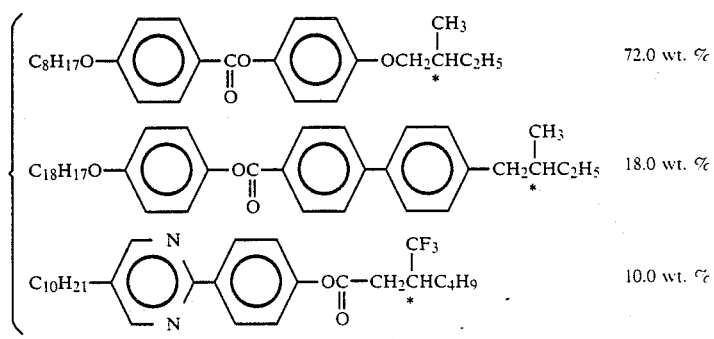

<Composition C>

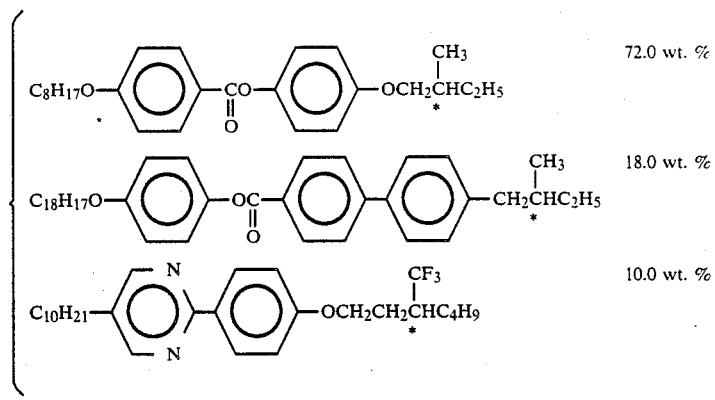

TABLE 5

Phase transition temperature of liquid crystal compositions

| Composition (Example No.) | phase transition temperature (°C.) |
|---|---|
| A (19) | Cryst. $\underset{12}{\overset{14}{\rightleftarrows}}$ S₃ $\underset{14}{\overset{16}{\rightleftarrows}}$ S$_C$* $\underset{45}{\overset{46}{\rightleftarrows}}$ S$_A$ $\underset{64}{\overset{65}{\rightleftarrows}}$ Ch. $\underset{71}{\overset{72}{\rightleftarrows}}$ Iso. |
| B (20) | Cryst. $\underset{10}{\overset{11}{\rightleftarrows}}$ S$_C$* $\underset{41}{\overset{42}{\rightleftarrows}}$ S$_A$ $\underset{60}{\overset{61}{\rightleftarrows}}$ Ch. $\underset{68}{\overset{68}{\rightleftarrows}}$ Iso. |
| C (21) | Cryst. $\underset{7}{\overset{16}{\rightleftarrows}}$ S$_C$* $\underset{40}{\overset{41}{\rightleftarrows}}$ S$_A$ $\underset{59}{\overset{60}{\rightleftarrows}}$ Ch. $\underset{67}{\overset{66}{\rightleftarrows}}$ Iso. |

TABLE 5-continued

Phase transition temperature of liquid crystal compositions

| Composition (Example No.) | phase transition temperature (°C.) |
|---|---|
| M (Comparative) | Cryst. $\underset{18}{\overset{20}{\rightleftarrows}}$ S$_C^*$ $\underset{52}{\overset{53}{\rightleftarrows}}$ S$_A$ $\underset{64}{\overset{65}{\rightleftarrows}}$ Ch. $\underset{75}{\overset{76}{\rightleftarrows}}$ Iso. |

TABLE 6

Spontaneous polarization (nC/cm$^2$)

| Temp. (°C.) | Composition (Ex. No.) | | | |
|---|---|---|---|---|
| | A (19) | B (20) | C (21) | M (comp.) |
| 40 | 2.1 | — | — | 1.2 |
| 35 | — | 5.5 | 3.3 | 1.9 |
| 25 | 3.2 | 8.0 | 4.9 | 2.5 |

TABLE 7

Optical response time (msec)

| Temp. (°C.) | Composition (Ex. No.) | | | |
|---|---|---|---|---|
| | A (19) | B (20) | C (21) | M (comp.) |
| 40 | 0.15 | — | — | 0.55 |
| 35 | — | 0.08 | 0.14 | 0.69 |
| 25 | 0.71 | 0.18 | 0.33 | 1.28 |

EXAMPLE 22

A glass substrate provided with an ITO (indium tin oxide) transparent electrode film was coated with a polyimide resin precursor (SP-510, mfd. by Toray K. K.), followed by heating at 300° C. for 60 min. to form a polyimide film. Then, the film was orientation-treated by rubbing. Two glass substrates thus treated were fixed to each other so that their rubbing treated axes crossed each other at right angles, thereby to form a blank cell with a cell gap of 8 μm. The cell was filled with a nematic liquid crystal composition (Lixon GR-63, a biphenyl liquid crystal mixture available from Chisso K. K.) to form a TN (twisted nematic)-type cell. When observed through a polarizing microscope, the TN-type cell showed a fringe pattern due to occurrence of reverse domain.

A liquid crystal composition was prepared by adding 1 wt. part of the mesomorphic compound obtained by the above Example 2 to 99 wt. parts of the above Lixon GR-63 and used for preparation of a TN cell in the same manner as above. As a result of observation through a polarizing microscope, no reverse domain was observed but a uniform nematic phase was observed in the TN cell. From this fact, the mesomorphic compound of the invention was found to be effective for prevention of reverse domain.

EXAMPLE 23

A liquid crystal composition D as shown below containing the mesomorphic compound of Example 11 was prepared. The phase transition temperature of the composition D was also shown below. Further, the spontaneous polarization and optical response time of the liquid crystal composition D as measured in the same manner as in Example 19 are also shown below together with the above-mentioned Composition M which has the same composition as the Composition D except for the omission of the mesomorphic compound of Example 11.

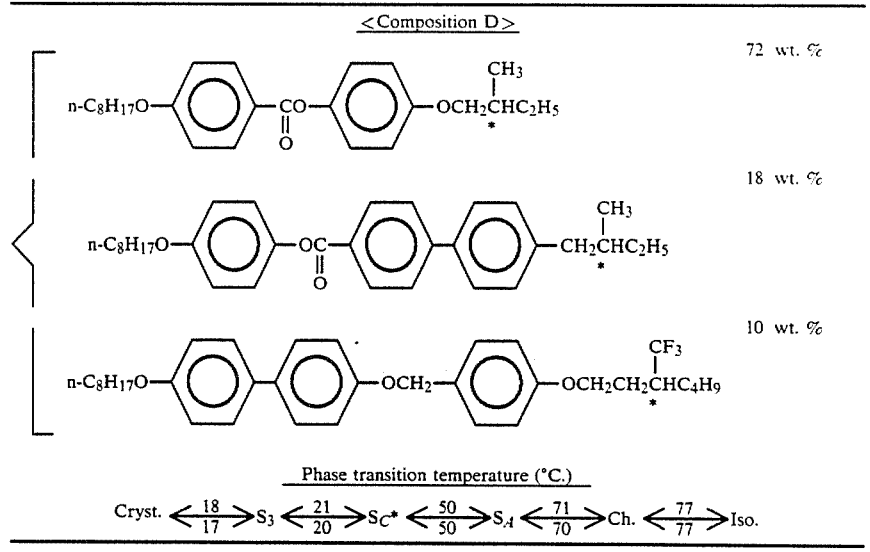

<Composition D>

Phase transition temperature (°C.)

Cryst. $\underset{17}{\overset{18}{\rightleftarrows}}$ S$_3$ $\underset{20}{\overset{21}{\rightleftarrows}}$ S$_C^*$ $\underset{50}{\overset{50}{\rightleftarrows}}$ S$_A$ $\underset{70}{\overset{71}{\rightleftarrows}}$ Ch. $\underset{77}{\overset{77}{\rightleftarrows}}$ Iso.

| Temp. (°C.) | Composition D | Composition M |
|---|---|---|
| | Spontaneous polarization (nC/cm$^2$) | |
| 40 | 5.4 | 1.2 |
| 30 | 7.7 | 2.0 |
| | Optical response time (msec) | |
| 40 | 0.091 | 0.55 |
| 30 | 0.20 | 0.93 |

EXAMPLE 24

A liquid crystal composition was prepared by adding 1 wt. part of the mesomorphic compound of Example 11 to 99 wt. parts of Lixon GR-63 and used for preparation of a TN cell in the same manner as in Example 22. As a result of observation through a polarizing microscope, no reverse domain was observed but a uniform nematic phase was observed in the TN cell, so that the above mesomorphic compound was found to be effective for prevention of reverse domain.

EXAMPLE 25

A liquid crystal composition as shown below containing the mesomorphic compound ⑥ (Example Compound (72)) prepared in Example 14 was prepared by mixing the respective compound in proportions shown.

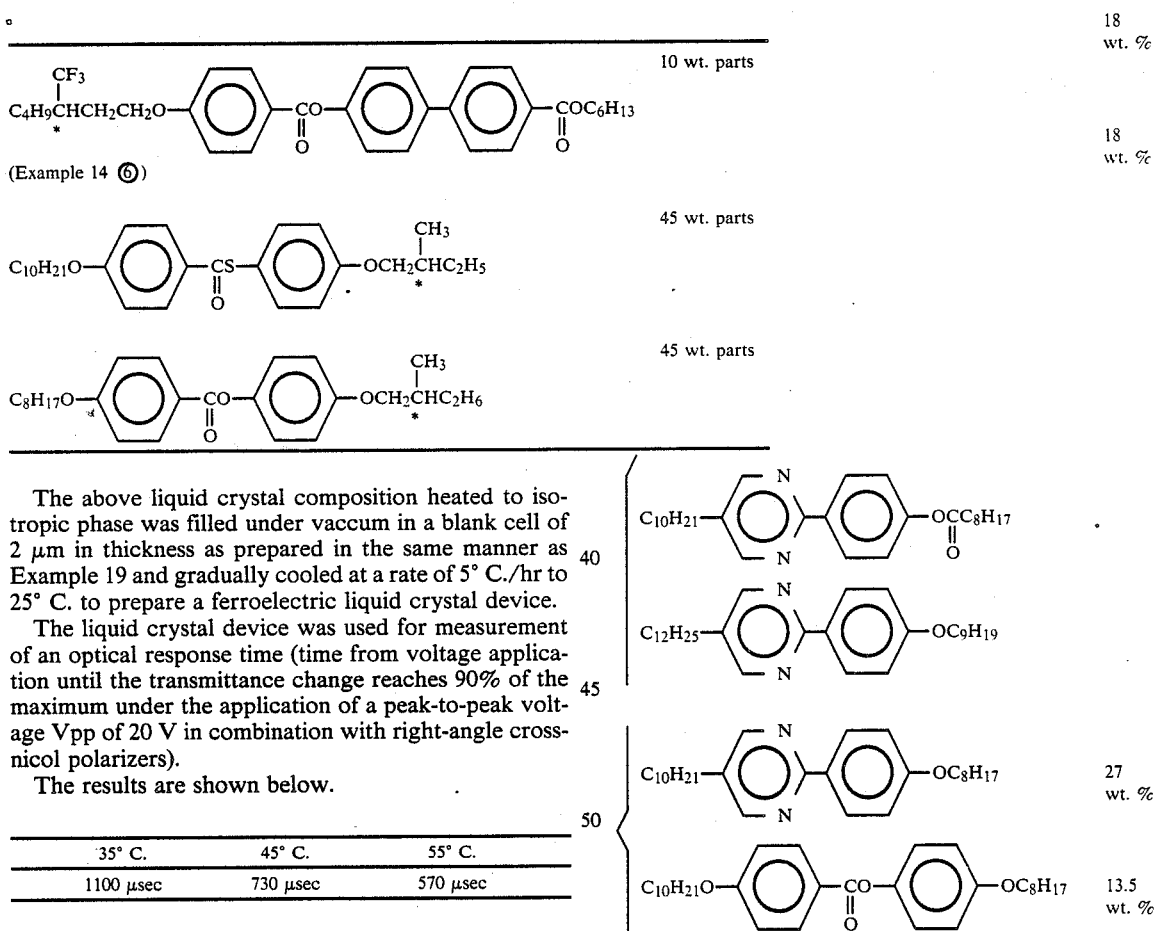

The above liquid crystal composition heated to isotropic phase was filled under vaccum in a blank cell of 2 μm in thickness as prepared in the same manner as Example 19 and gradually cooled at a rate of 5° C./hr to 25° C. to prepare a ferroelectric liquid crystal device.

The liquid crystal device was used for measurement of an optical response time (time from voltage application until the transmittance change reaches 90% of the maximum under the application of a peak-to-peak voltage Vpp of 20 V in combination with right-angle crossnicol polarizers).

The results are shown below.

| 35° C. | 45° C. | 55° C. |
|---|---|---|
| 1100 μsec | 730 μsec | 570 μsec |

COMPARATIVE EXAMPLE 1

A ferroelectric liquid crystal device was prepared in the same manner as in Example 25 except that the mesomorphic compound ⑥ used in Example 25 was omitted from the ferroelectric liquid crystal composition used and used for measurement of the optical response time in the same manner as in Example 25. The results are shown below.

| 35° C. | 45° C. | 50° C. |
|---|---|---|
| 1500 μsec | 1000 μsec | 800 μsec |

EXAMPLE 26

A liquid crystal composition was prepared by adding 1 wt. part of the mesomorphic compound of Example 14 to 99 wt. parts of Lixon GR-63 and used for preparation of a TN cell in the same manner as in Example 22. As a result of observation through a polarizing microscope, no reverse domain was observed but a uniform nematic phase was observed in the TN cell.

EXAMPLE 27

A liquid crystal composition E as shown below containing Example Compound (27) was prepared.

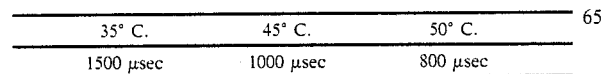

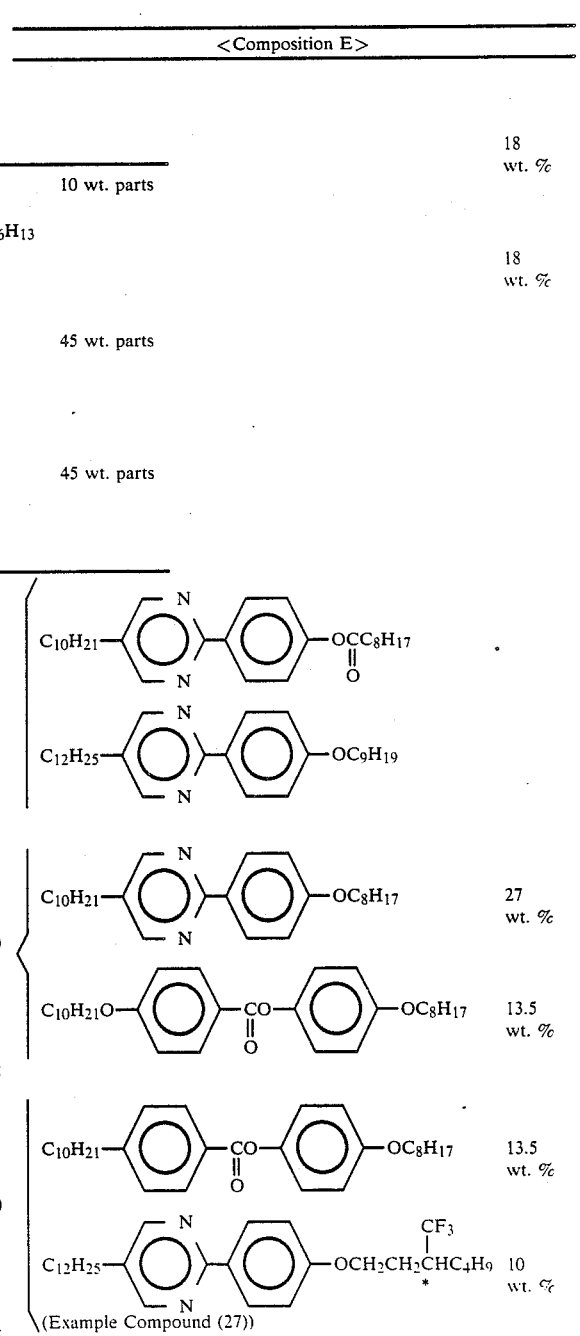

The phase transition temperatures, spontaneous polarization and optical response time of the liquid crystal composition E prepared in the same manner as in Example 19 are shown below.

| Phase transition temperature (°C.) | |
|---|---|
| Cryst. ←4— $S_{C^*}$ ←42— $S_A$ ←65— Iso. | |
| Spontaneous polarization (nC/cm$^2$) | |
| 40° C. | 30° C. |
| 4.1 | 5.1 |
| Optical response time | |
| 40° C. | 30° C. |
| 16 μsec | 22 μsec |

Thus, a liquid crystal composition showing a fast optical response was obtained by inclusion of a compound having an optically active trifluoromethyl group.

As described above, according to the present invention, there is provided a mesomorphic compound showing a good electric field-responsive characteristic. Further, a liquid crystal composition containing the mesomorphic compound and a liquid crystal device containing the liquid crystal composition show not only an improved response speed but also an excellent effect of preventing occurrence of reverse domain.

What is claimed is:

1. An optically active compound represented by the following formula (I):

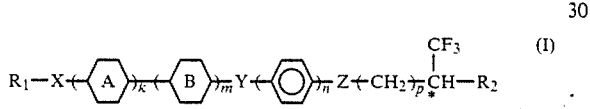

wherein $R_1$ denotes an alkyl group having 1-18 carbon atoms, $R_2$ denotes an alkyl group having 1-12 carbon atoms; X denotes a single bond, —O—,

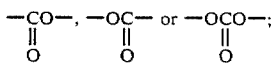

Y denotes a single bond,

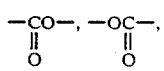

—CH$_2$O— or —OCH$_2$—; Z denotes —OCH$_2$—,

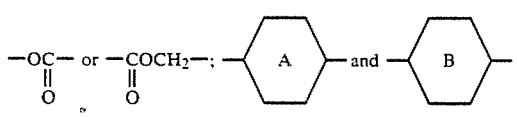

independently denote

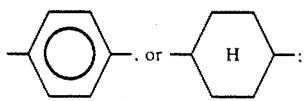

C* denotes an asymmetric carbon atom; k, m and n are independently 0, 1 or 2 with proviso that k+m+n is 2 or 3; and p is 1 or 2.

2. A compound according to claim 1, which is represented by the following formula (I-a):

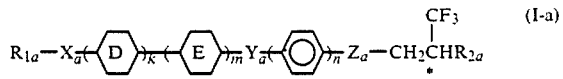

wherein $R_{1a}$ denotes an alkyl group having 4-16 carbon atoms, $R_{2a}$ denotes an alkyl group having 1-12 carbon atoms; k, m and n are independently 0, 1 or 2 with proviso that k+m+n is 2 or 3; $X_a$ denotes a single bond; $Y_a$ denotes a single bond or

Za denotes —OCH$_2$—,

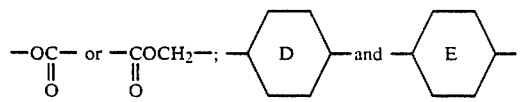

independently denote

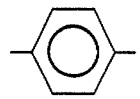

and C* denotes an asymmetric carbon atom.

3. A compound according to claim 1, which is represented by the following formula (I-b):

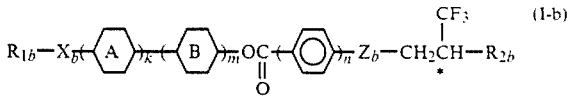

wherein $R_{1b}$ denotes an alkyl group having 1-18 carbon atoms, $R_{2b}$ denotes an alkyl group having 1-12 carbon atoms; $X_b$ denotes a single bond, —O—,

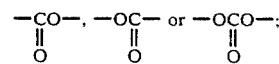

$Z_b$ denotes —OCH$_2$— or

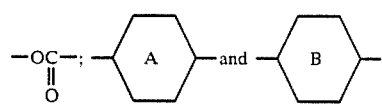

independently denote

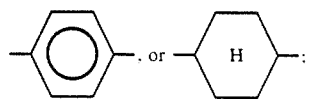

k, m and n are independently 0, 1 or 2 with proviso that k+m+n is 2 or 3; and C* denotes an asymmetric carbon atom.

4. A compound according to claim 1, which is represented by the following formula (I-c):

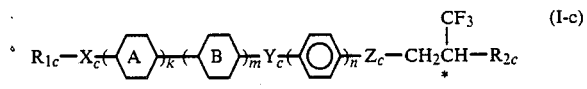 (I-c)

wherein $R_{1c}$ denotes an alkyl group having 1–18 carbon atoms, $R_{2c}$ denotes an alkyl group having 1–12 carbon atoms; $X_c$ denotes a single bond, —O—,

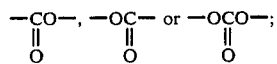

$Y_c$ denotes —CH$_2$O— or —OCH$_2$—; $Z_c$ denotes —OCH$_2$— or

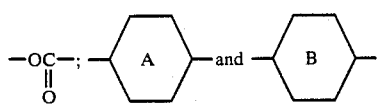

independently denotes

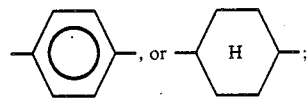

C* denotes an asymmetric carbon atom; and k, m and n are independently 0, 1 or 2 with proviso that k+m+n is 2 or 3.

5. A compound according to claim 1, which is a compound yielding a liquid crystal phase.

6. A compound according to claim 5, wherein said liquid crystal phase includes a smectic phase.

7. A compound according to claim 6, wherein said smectic phase includes smectic A phase.

8. A compound according to claim 6, wherein said smectic phase includes chiral smectic C phase.

9. A compound according to claim 5, wherein said liquid crystal phase includes chiral smectic C phase and cholesteric phase.

10. A compound according to claim 1, which is a compound not yielding a liquid crystal phase.

* * * * *

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

It is certified that error appears in the above-identified patent and that said Letters Patent is hereby corrected as shown below: ON TITLE PAGE:

AT [30] FOREIGN APPLICATION PRIORITY DATA

"63-071034" should read --63-071035-- and
insert --Jul. 6, 1988 [JP] Japan.....63-166781--.

AT [57] ABSTRACT

"respectively" should read --independently-- and
"amounts to" should read --is--.

COLUMN 1

Line 68, "while" should read --although--.

COLUMN 2

Line 26, ", as" should read --known--.
Line 33, "seldome" should read --seldom possible--.

COLUMN 4

Line 49, "denotes" should read --denote--.

COLUMN 8

Line 8, "denotes" should read --denote--.

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

It is certified that error appears in the above-identified patent and that said Letters Patent is hereby corrected as shown below:

COLUMN 3

Lines 1-20, "-OC- or -COCH$_2$-; -(A)- and -(B)-
 |         |
 O         O

-CH$_2$O- or -OCH$_2$-; Z denotes -OCH$_2$-,

-(O)-, -(O)- (with N's) or -(H)-;

respectively denotes
-CO-, -OC-,"
 |      |
 O      O should read

---CO-, -OC-, -CH$_2$O- or
   |    |
   O    O

-OCH$_2$-; Z denotes -OCH$_2$-, -OC- or -COCH$_2$-;
                                |         |
                                O         O -(A)- and -(B)- respectively denote -(O)-, -(O)- (with N's) or -(H)-; --.

Line 26, "optically active" should read
--optically active compound--.

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

Page 3 of 13

It is certified that error appears in the above-identified patent and that said Letters Patent is hereby corrected as shown below:

COLUMN 15

Line 18, Cont'd.

(56) 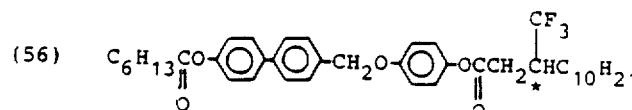

(57) 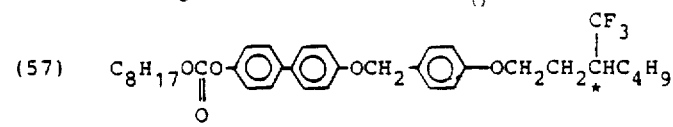

(58) 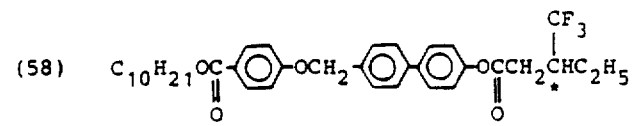

(59) 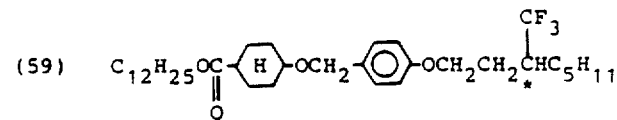

(60) 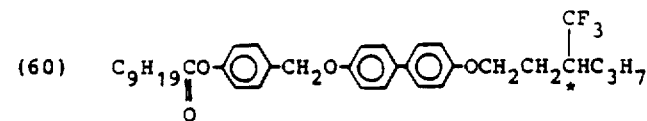

(61) 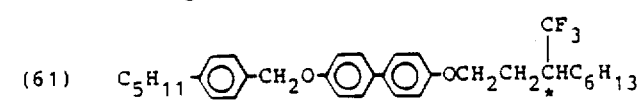

(62) 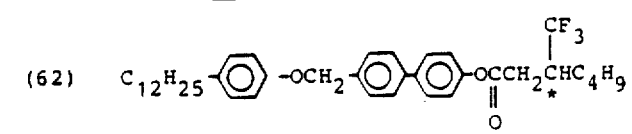

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

Page 4 of 13

It is certified that error appears in the above-identified patent and that said Letters Patent is hereby corrected as shown below:

COLUMN 15

Line 18, Cont'd.

(63) 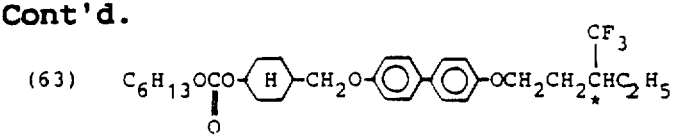

(64) 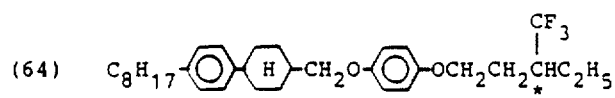

(65) 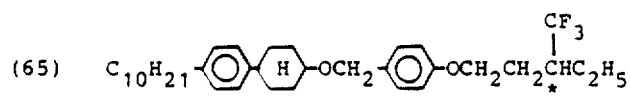

(66) 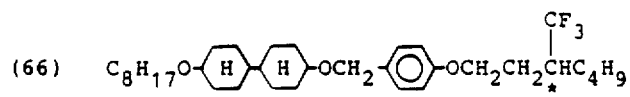

(67) 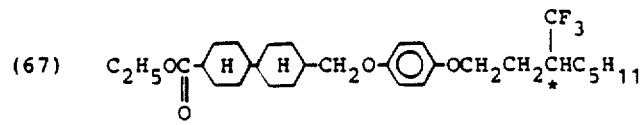

(68) 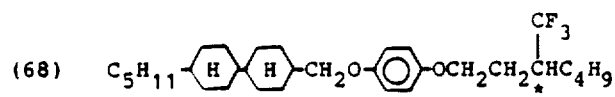

(69) 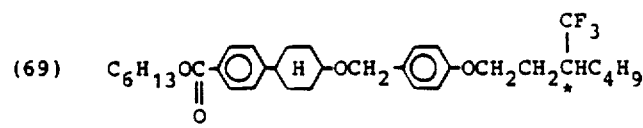

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

Page 5 of 13

It is certified that error appears in the above-identified patent and that said Letters Patent is hereby corrected as shown below:

COLUMN 15

Line 18, Cont'd.

(70)

(71) 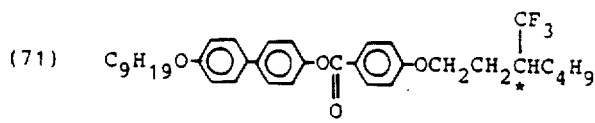

(72) 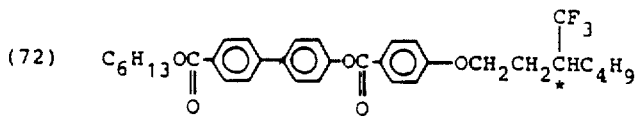

(73) 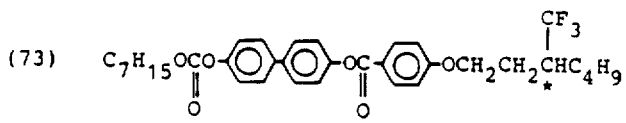

(74) 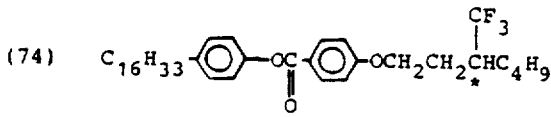

(75) 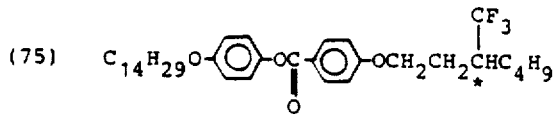

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

It is certified that error appears in the above-identified patent and that said Letters Patent is hereby corrected as shown below:

COLUMN 15

Line 18, Cont'd.

(76) 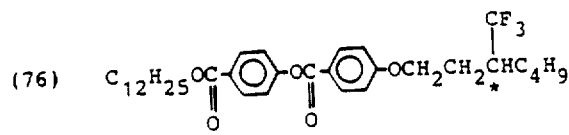

(77) 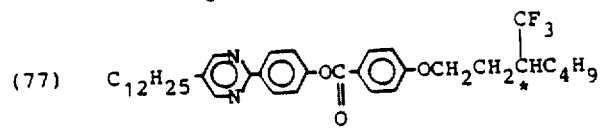

(78) 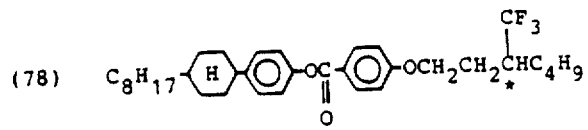

(79) 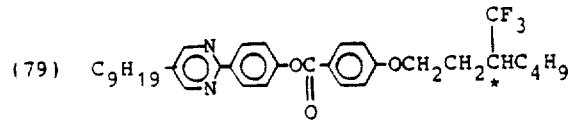

(80) 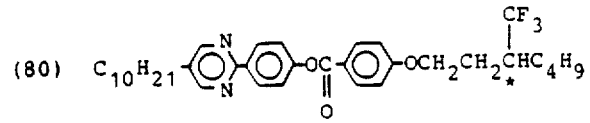

(81) 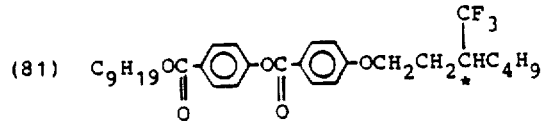

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

It is certified that error appears in the above-identified patent and that said Letters Patent is hereby corrected as shown below:

COLUMN 15

Line 18, Cont'd.

(82) 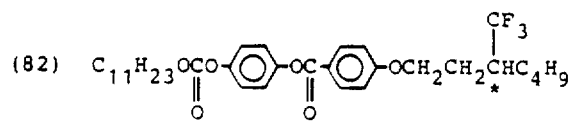

(83) 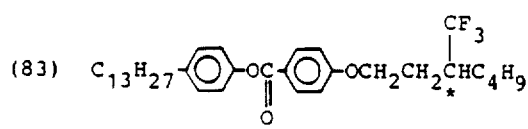

(84) 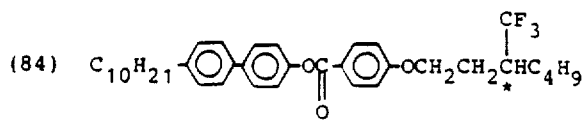

(85) 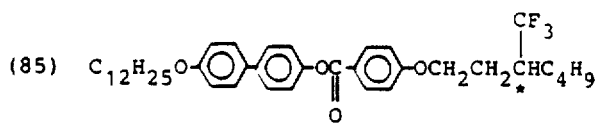

(86) 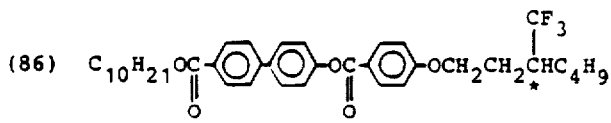

(87) 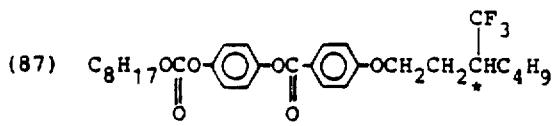

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

It is certified that error appears in the above-identified patent and that said Letters Patent is hereby corrected as shown below:

COLUMN 15

Line 18, Cont'd.

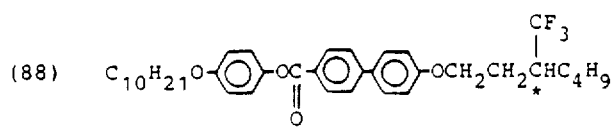

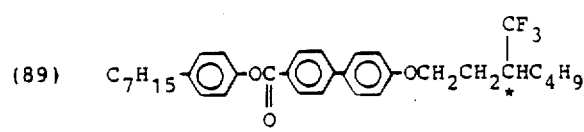

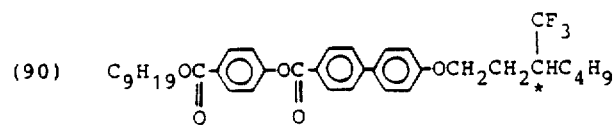

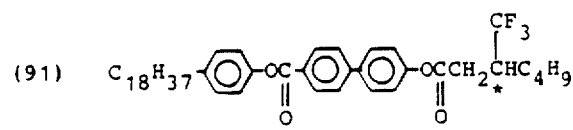

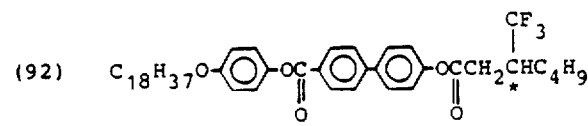

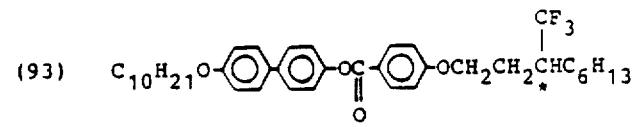

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

It is certified that error appears in the above-identified patent and that said Letters Patent is hereby corrected as shown below:

COLUMN 15

Line 18, Cont'd.

(94) 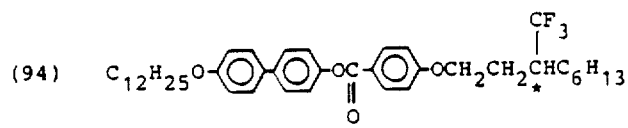

(95) 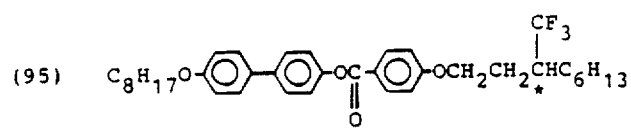

(96) 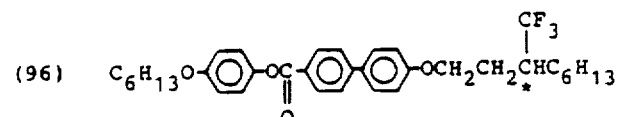

(97) 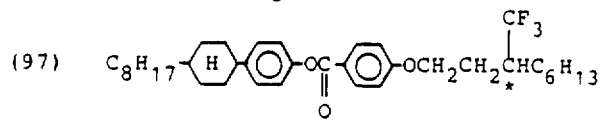

(98) 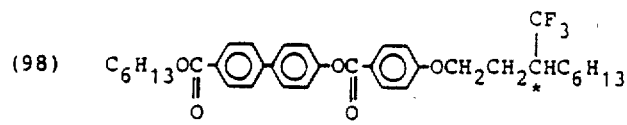

(99) 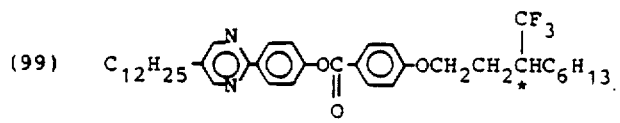

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

Page 10 of 13

It is certified that error appears in the above-identified patent and that said Letters Patent is hereby corrected as shown below:

COLUMN 15

Line 18, Cont'd.

(100) 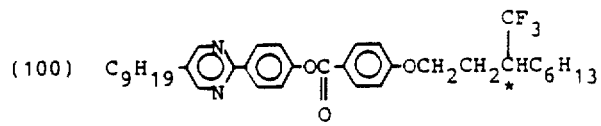

(101) 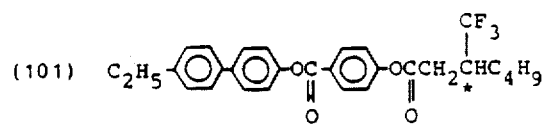

(102) 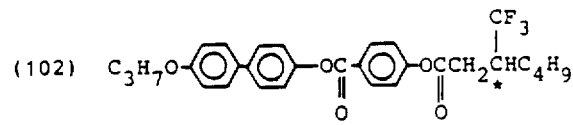

(103) 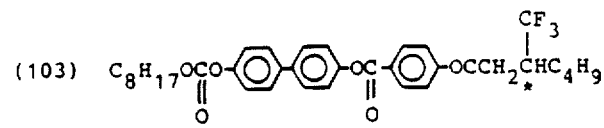

(104) 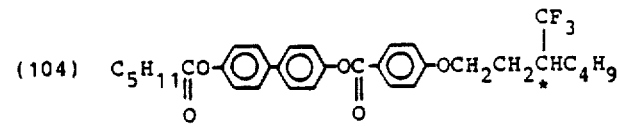

(105) 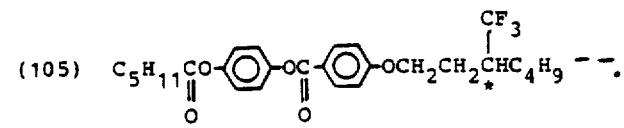

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.

It is certified that error appears in the above-identified patent and that said Letters Patent is hereby corrected as shown below:

COLUMN 16

Line 21, "resent" should read --represented--.

COLUMN 21

Line 15, "4,4'-decyloxyazoybenzene" should read ----4,4'-decyloxyazoxybenzene--.

COLUMN 22

Lines 41-45,  should read

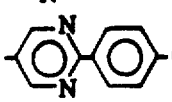 (5)--.

COLUMN 24

Line 16, "$CH_2Cl_2$)," should read --$CH_2Cl_2$).--.
Line 22, "was" (first occurrence) should read --were--.
Line 40, "chomatography" should read --chromatography--.

COLUMN 25

Line 22, "$CH_2Cl_2$)," should read --$CH_2Cl_2$).--.
Line 46, "$CH_2Cl_2$)," should read --$CH_2Cl_2$).--.
Line 50, "compound (31))" should read --compound (31)).--.

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.        Page 12 of 13

It is certified that error appears in the above-identified patent and that said Letters Patent is hereby corrected as shown below:

COLUMN 26

Line 23, "$CH_2Cl_2$)," should read --$CH_2Cl_2$).--.
Line 27, "compound (25))," should read --compound (25)).--.
Line 38, ""$CH_2Cl_2$)," should read --$CH_2Cl_2$).--.
Line 43, "(18))," should read --(18)).--.
Line 59, "Iso. isotropic liquid;" should read
        --Iso., isotropic liquid;--.

COLUMN 27

Table 1,  "$[α]_D^{24}$+8.1"  should read  --$[α]_D^{24}$+8.1--.
        (c1,CH|$Cl_2$)                (c1,$CH_2Cl_2$)

COLUMN 31

Line 10, "dired" should read --dried--.
Line 11, "on" should read --with--.

COLUMN 35

Table 2, "      $CF_3$       "   should read --       $CF_3$      --.
                |                                    |
        O($CH_2$)$_3$CHC$_4$H|                O($CH_2$)$_3$CHC$_4$H$_9$
              *                                       *

COLUMN 40

Line 42, "P'-octylbiphenyl p-" should read
        --p-octylbiphenyl p'---.

UNITED STATES PATENT AND TRADEMARK OFFICE
CERTIFICATE OF CORRECTION

PATENT NO. : 4,918,213
DATED : April 17, 1990
INVENTOR(S) : HIROYUKI NOHIRA ET AL.     Page 13 of 13

It is certified that error appears in the above-identified patent and that said Letters Patent is hereby corrected as shown below:

COLUMN 57

Line 24, "denotes" should read --denote--.

COLUMN 56

Lines 27-30, "" should read --;--.

COLUMN 47

Line 55, "pH 2" should read --pH 2 was reached--.

COLUMN 53

Line 39, "as" (first occurrence) should read --and-- and --as-- (second occurrence) should read --as in--.

Signed and Sealed this

Seventh Day of July, 1992

Attest:

DOUGLAS B. COMER

Attesting Officer     Acting Commissioner of Patents and Trademarks